US009725473B2

(12) United States Patent
Vankayalapati et al.

(10) Patent No.: US 9,725,473 B2
(45) Date of Patent: Aug. 8, 2017

(54) ANTHRACENE-9, 10-DIONE DIOXIME COMPOUND PRODRUGS AND THEIR USES

(71) Applicant: Beta Cat Pharmaceuticals, Inc.

(72) Inventors: Hariprasad Vankayalapati, Draper, UT (US); Xiaohui Liu, Holladay, UT (US); Sunil Sharma, Salt Lake City, UT (US); Srinivas Rao Kasibhatla, San Diego, CA (US); Seelam Venkata Reddy, Telangana (IN)

(73) Assignee: Beta Cat Pharmaceuticals, Inc., Houston, TX (US)

( * ) Notice: Subject to any disclaimer, the term of this patent is extended or adjusted under 35 U.S.C. 154(b) by 0 days.

(21) Appl. No.: 15/222,556

(22) Filed: Jul. 28, 2016

(65) Prior Publication Data
US 2017/0029450 A1     Feb. 2, 2017

Related U.S. Application Data

(60) Provisional application No. 62/197,973, filed on Jul. 28, 2015.

(51) Int. Cl.
| *A61K 31/4545* | (2006.01) |
| *A61K 31/675* | (2006.01) |
| *A61K 45/06* | (2006.01) |
| *C07D 211/96* | (2006.01) |
| *C07F 9/553* | (2006.01) |
| *C07F 9/59* | (2006.01) |

(52) U.S. Cl.
CPC ........ *C07F 9/5532* (2013.01); *A61K 31/4545* (2013.01); *A61K 31/675* (2013.01); *A61K 45/06* (2013.01); *C07D 211/96* (2013.01); *C07F 9/591* (2013.01)

(58) Field of Classification Search
CPC .... C07F 9/5532; C07F 9/591; A61K 31/4545; A61K 31/675; A61K 45/06; C07D 311/96
USPC .......................................................... 514/89
See application file for complete search history.

(56) References Cited

U.S. PATENT DOCUMENTS

2013/0143920 A1* 6/2013 Bhalla ................ A61K 31/4545
                                                                    514/316

* cited by examiner

*Primary Examiner* — Yevegeny Valenrod
(74) *Attorney, Agent, or Firm* — Wood, Phillips, Katz, Clark & Mortimer

(57) ABSTRACT

Chemical agents, such as disulfonamide derivatives of fluorene, anthracene, xanthene, dibenzosuberone and acridine, and similar heterocyclic ring structures; including, salts thereof that act as anti-cancer and anti-tumor agents, along with methods for preparing such agents, as well as pharmaceutical compositions containing such agents as active ingredients and methods of using these as therapeutic agents.

21 Claims, No Drawings

ANTHRACENE-9, 10-DIONE DIOXIME COMPOUND PRODRUGS AND THEIR USES

FIELD OF THE INVENTION

The present invention relates to novel prodrugs of biologically active anthracene-9, 10-dione dioxime compounds, their intermediates, methods for synthesizing, and their use to treat cancer and other diseases.

BACKGROUND OF THE INVENTION

Cancer is the second leading cause of death in the United States. It presents complex challenges for the development of new therapies. Cancer is characterized by the abnormal growth of malignant cells that have undergone a series of genetic changes that lead to growth of tumor mass and metastatic properties.

Beta-catenin (β-catenin) is part of a complex of proteins that constitute adherens junctions (AJs). AJs are necessary for the creation and maintenance of epithelial cell layers by regulating cell growth and adhesion between cells. β-catenin also anchors the actin cytoskeleton and may be responsible for transmitting the contact inhibition signal that causes cells to stop dividing once the epithelial sheet is complete.

Wnt/β-catenin pathway has been shown to play a role in cancer. Aberrant β-catenin signaling plays an important role in tumorigenesis. In particular, colorectal cancer is estimated to have greater than 80% mutations in the β-catenin pathway, leading to unregulated oncogenic signaling. Aberrant β-catenin signaling has been shown to be involved in various cancer types, including melanoma, breast, lung, colon, liver, gastric, myeloma, multiple myeloma, chronic myelogenous leukemia, chronic lymphocytic leukemia, T-cell non-Hodgkin lymphomas, colorectal and acute myeloid leukemia (AML) cancers. Further, aberrant Wnt/β-catenin signaling has been found in a large number of other disorders, including osteoporosis, osteoarthritis, polycystic kidney disease, diabetes, schizophrenia, vascular disease, cardiac disease, hyperproliferative disorders, and neurodegenerative diseases. Myeloproliferative neoplasms (MPNs) are a closely related group of hematological malignancies in which the bone marrow cells that produce the body's blood cells develop and function abnormally. The three main myeloproliferative neoplasms are Polycythemia Vera (PV), Essential Thrombocythemia (ET) and Primary Myelofibrosis (PMF). A gene mutation in JAK2 is present in most PV patients and 50% of ET and PMF patients. The beta catenin pathway is activated in MPN in many cases and required for survival of these cells.

While some anthracene-9, 10-dione dioxime compounds are known, there is a still need for novel compounds that are able interrupt the Wnt/β-catenin pathway and inhibit the deregulated activity of this pathway for the treatment, diagnosis and prevention of β-catenin pathway-related disorders and diseases.

SUMMARY OF THE INVENTION

The invention relates to novel prodrugs of the biologically active anthracene-9, 10-dione dioxime compounds, their intermediates, methods for synthesizing, and their use to treat cancer and other diseases.

The invention also includes pharmaceutically acceptable salts, polymorphs, geometric isomers, stereoisomers, enantiomers, diastereomers, solvates, esters, tautomers and metabolites of the provided prodrugs.

Some non-limiting examples of pharmaceutically acceptable salts are the ammonium, calcium, magnesium, potassium, and sodium salts.

Also disclosed are pharmaceutical compositions comprising a therapeutically effective amount of a disclosed compound and a pharmaceutically acceptable carrier.

Also disclosed are synthetic methods for making the disclosed compounds. In a further aspect, disclosed are the products of the disclosed synthetic methods.

Also disclosed are methods for the treatment of a disorder associated with a Wnt/β-catenin pathway in a mammal comprising the step of administering to the mammal a therapeutically effective amount of a disclosed compound, or a pharmaceutically acceptable salt, hydrate, solvate, or polymorph thereof.

In one aspect, the invention provides the compounds of the following formula:

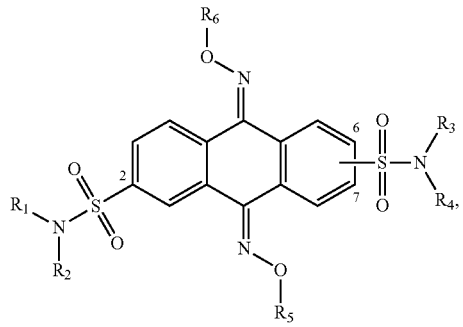

wherein $R_1$, $R_2$, $R_3$, and $R_4$ are each independently selected from H, alkyl, heteroalkyl, cycloalkyl, arylcycloalkyl, alkenyl, alkynyl, aryl, heteroaryl, heterocycloalkyl, and each of said $NR_1R_2$ and $NR_3R_4$ can independently combine to form a 6- to 15-membered heterocycloalkyl;

$R_5$ and $R_6$ are independently selected from the group consisting of H, —P(OXOH)$_2$, —CHR$_7$—O—P(O)(OH)$_2$, —C(O)—R$_8$, and —CHR$_7$—O—C(O)—R$_8$, $R_7$ is H or an optionally substituted lower alkyl;

$R_8$ is a lower alkyl, —OR$_{11}$, -aryl, heteroaryl or heterocycloalkyl, wherein said lower alkyl, aryl, heteroaryl or heterocycloalkyl is optionally substituted with —NR$_9$R$_{10}$ and/or OR$_{12}$;

$R_9$ and $R_{10}$ are independently selected from the group consisting of H, —P(O)(OH)$_2$, and optionally substituted lower alkyl;

$R_{11}$ is independently selected from the group consisting of lower alkyl, aryl, heteroaryl and heterocycloalkyl wherein said lower alkyl, aryl, heteroaryl or heterocycloalkyl is optionally substituted with —NR$_9$R$_{10}$ and/or —OH; and $R_{12}$ is H or —P(O)(OH)$_2$, or a polymorph, a geometric isomer, a stereoisomer, an enantiomer, a diastereomer, a solvate, an ester, a tautomer, a metabolite, or a pharmaceutically acceptable salt thereof.

In one preferred embodiment, the invention provides compounds wherein $NR_1R_2$ and $NR_3R_4$ are selected from

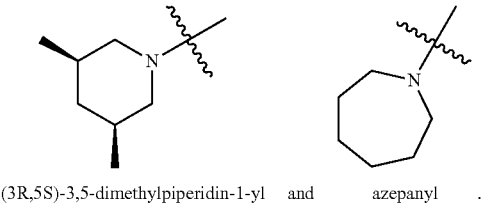

(3R,5S)-3,5-dimethylpiperidin-1-yl   and   azepanyl .

In another preferred embodiment, the invention provides compounds wherein $R_5$ is H.

In another preferred embodiment, the invention provides compounds wherein $R_5$ and $R_6$ are independently selected from the group consisting of H, and —P(O)(OH)$_2$.

In yet another preferred embodiment, the invention provides compounds wherein $R_5$ and $R_6$ are independently selected from the group consisting of H, —P(OXOH)$_2$, and —CHR$_7$—O—P(OXOH)$_2$.

In yet another preferred embodiment, the invention provides compounds wherein $R_6$ is —P(OXOH)$_2$.

In yet another preferred embodiment, the invention provides compounds wherein $NR_1R_2$ and $NR_3R_4$ are selected from

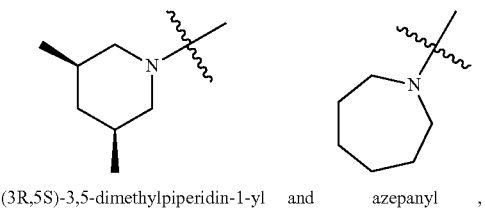

(3R,5S)-3,5-dimethylpiperidin-1-yl   and   azepanyl , and $R_5$ and $R_6$ are independently selected from the group consisting of H, —P(O)(OH)$_2$, and —CHR$_7$—O—P(O)(OH)$_2$.

In yet another preferred embodiment, the invention provides compounds wherein $R_5$ and $R_6$ are independently selected from the group consisting of H, —C(O)—R$_8$, and —CHR$_7$—O—C(O)—R$_8$.

In yet another preferred embodiment, the invention provides compounds wherein $NR_1R_2$ and $NR_3R_4$ are selected from

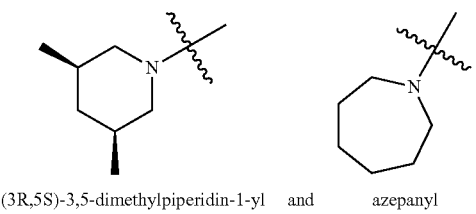

(3R,5S)-3,5-dimethylpiperidin-1-yl   and   azepanyl , and wherein $R_5$ and $R_6$ are independently selected from the group consisting of H, —C(O)—R$_8$, and —CHR$_7$—O—C(O)—R$_8$.

In yet another preferred embodiment, the invention provides compounds selected from the group consisting of

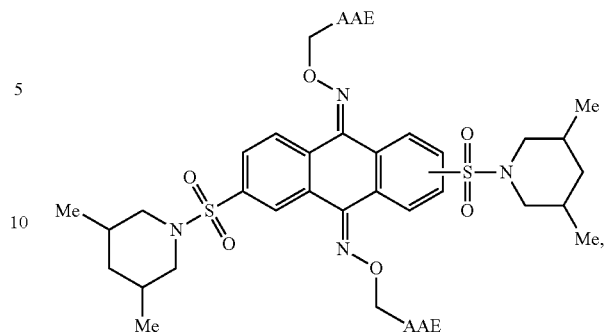

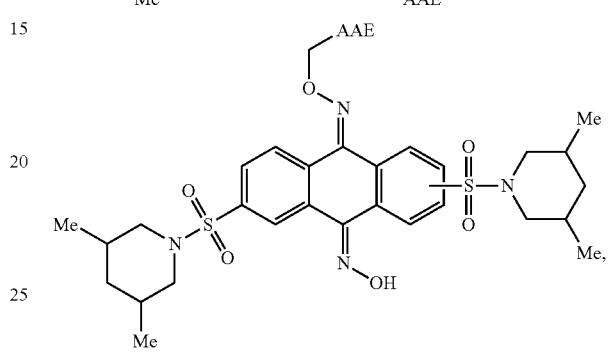

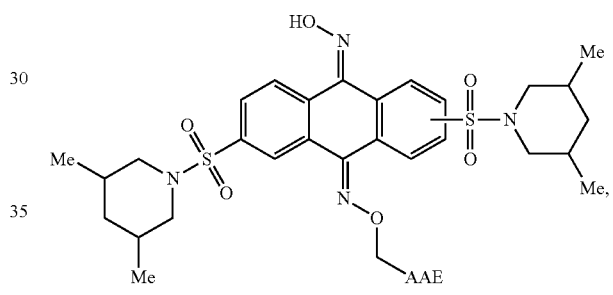

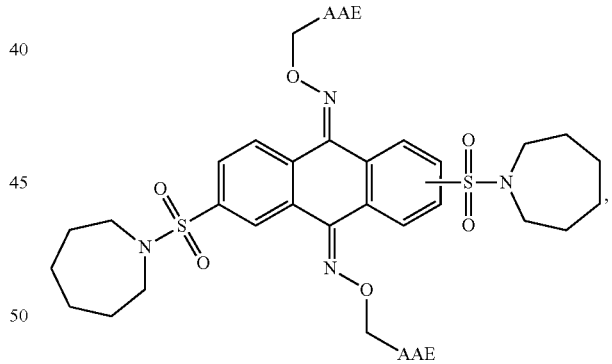

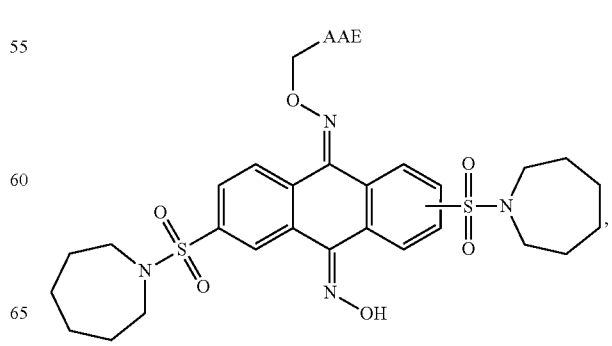

-continued

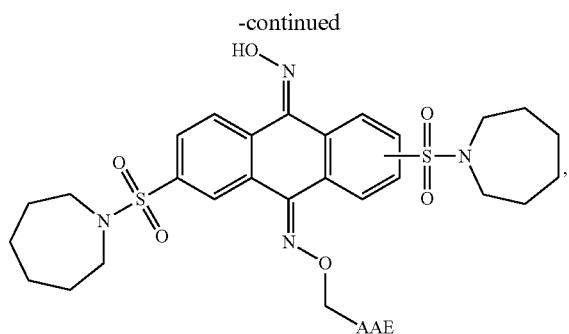

wherein AAE is an Amino Acid Ester selected from both natural and unnatural aminoacids.

In yet another preferred embodiment, the invention provides compounds selected from the group consisting of

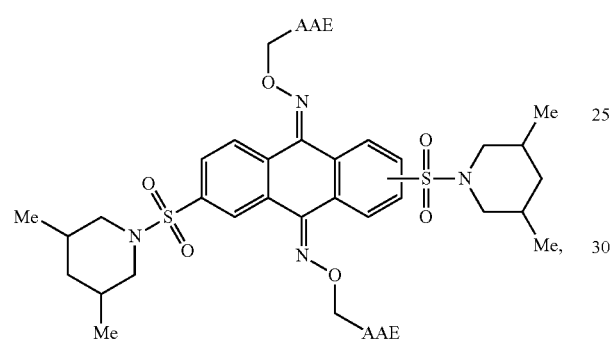

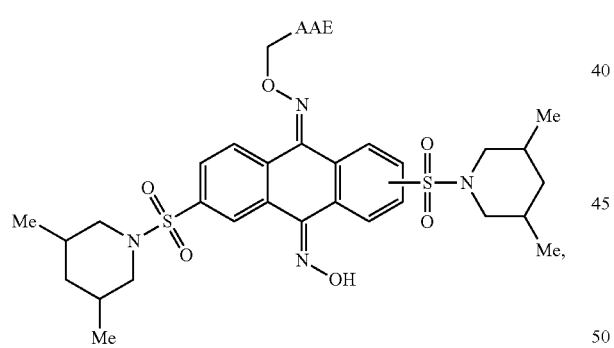

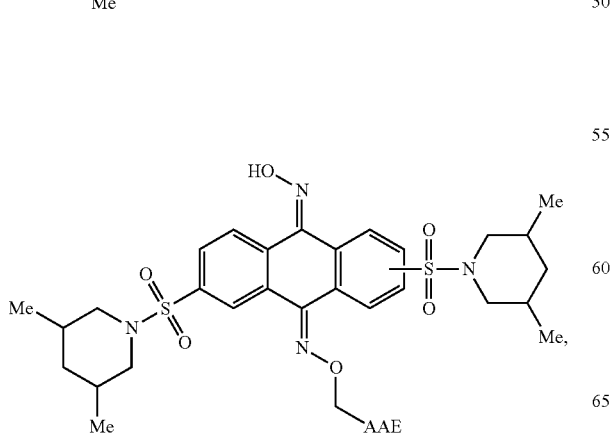

-continued

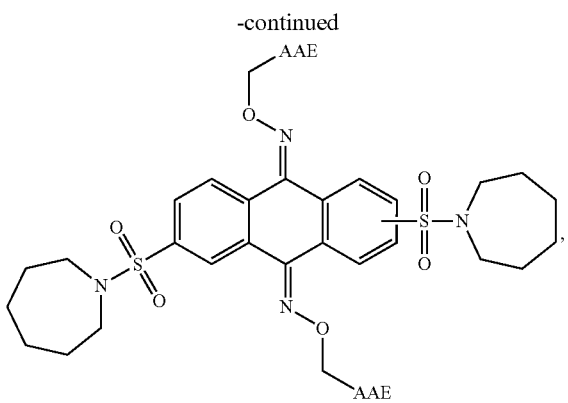

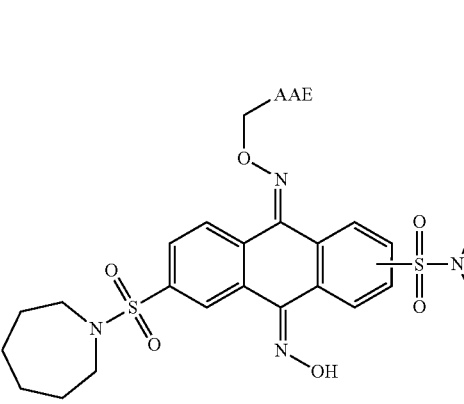

wherein AAE is selected from the group consisting of Glycine, L-Alanine, L-Valine, D-Valine, L-Serine, L-Cysteine, L-Leucine, L-Isoleucine, L-Lysine, L-Phenylalanine, L-Proline, L-Tyrosine and L-Serine.

In yet another preferred embodiment, the invention provides compounds selected from the group consisting of

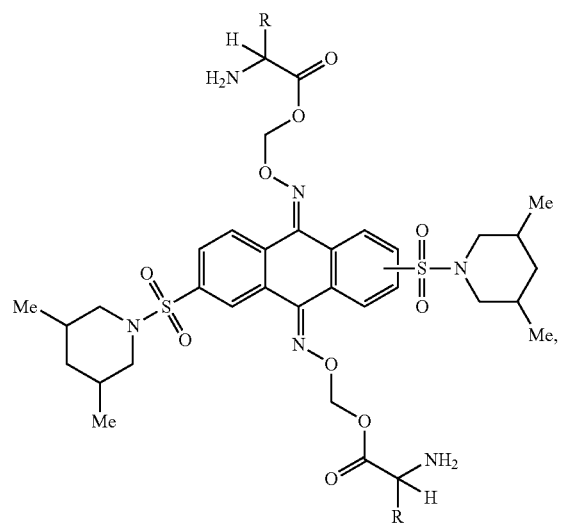

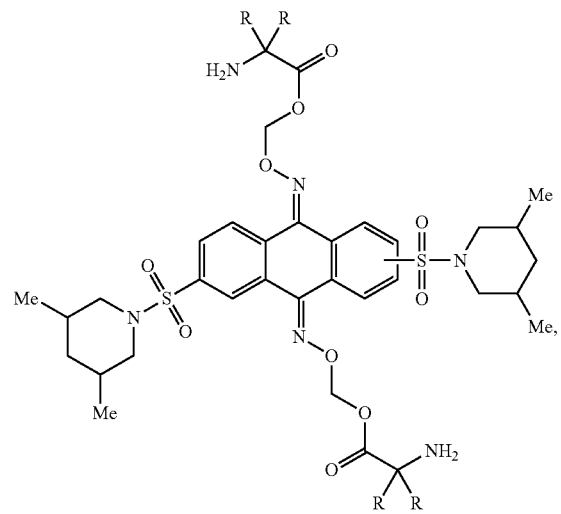

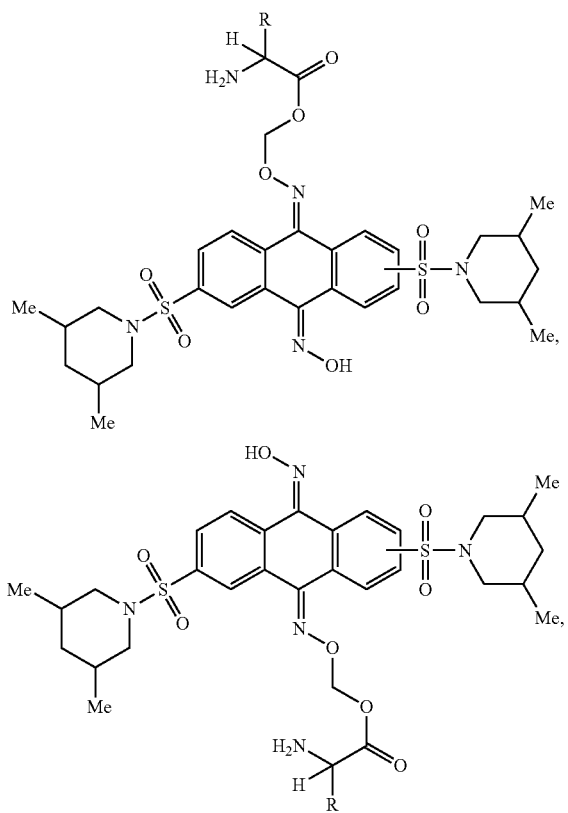

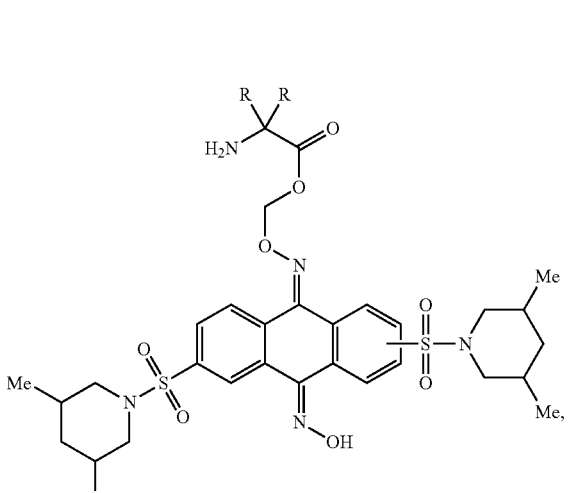

wherein R is selected from the group consisting of H, methyl, isopropyl, t-butyl, —CH$_2$OH, —CH$_2$CH(Me)$_2$, —CH(Me)CH$_2$CH$_3$, and

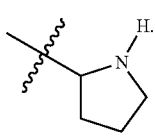

In yet another preferred embodiment, the invention provides compounds selected from the group consisting of wherein R is CH$_3$ or wherein R and R together form cyclopropyl group.

In yet another preferred embodiment, the invention provides compounds selected from the group consisting of

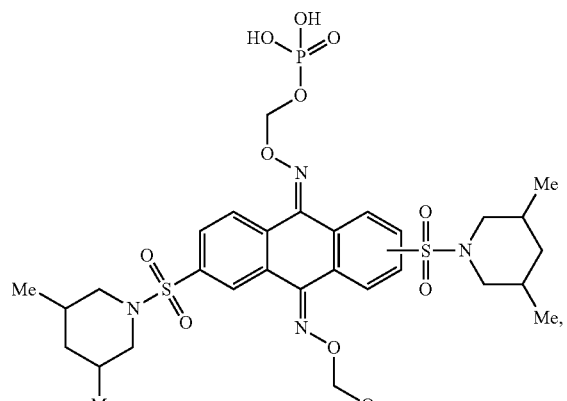
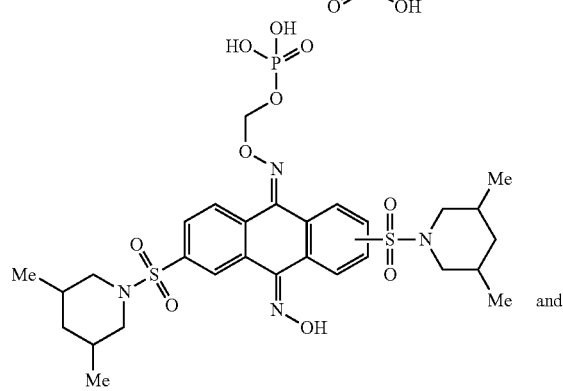
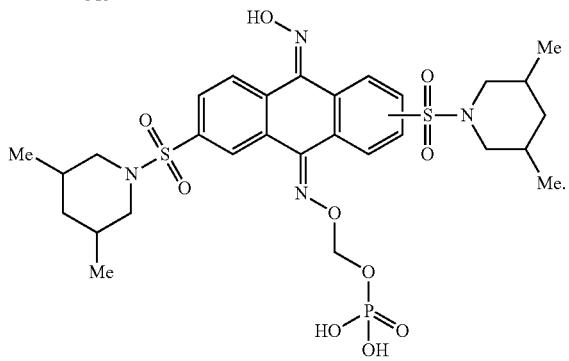
In yet another preferred embodiment, the invention provides compounds selected from the group consisting of
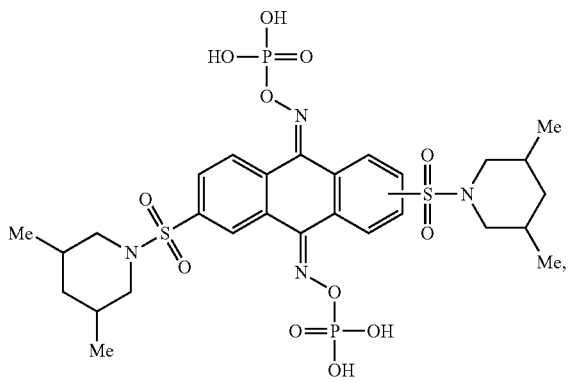
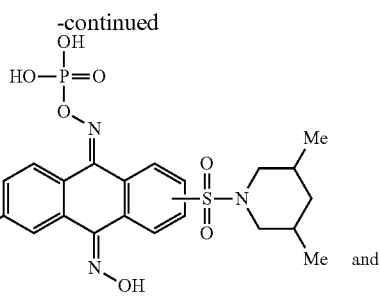
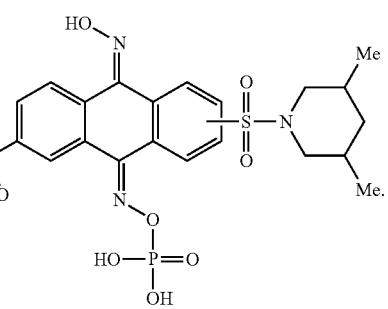
In yet another preferred embodiment, the invention provides compounds selected from the group consisting of
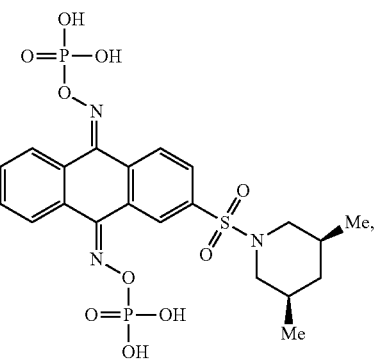
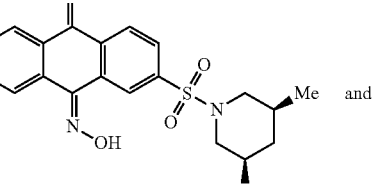

In yet another preferred embodiment, the invention provides compounds selected from the group consisting of

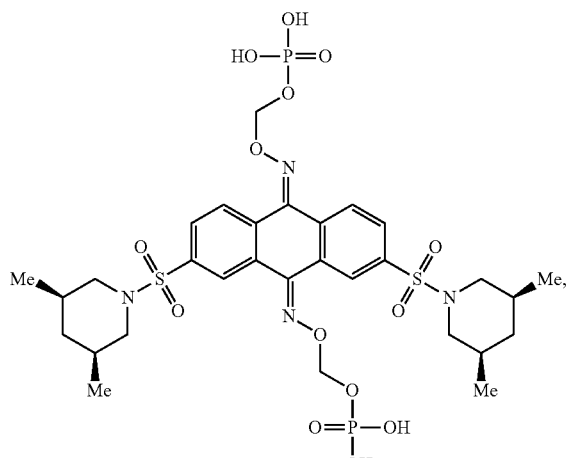

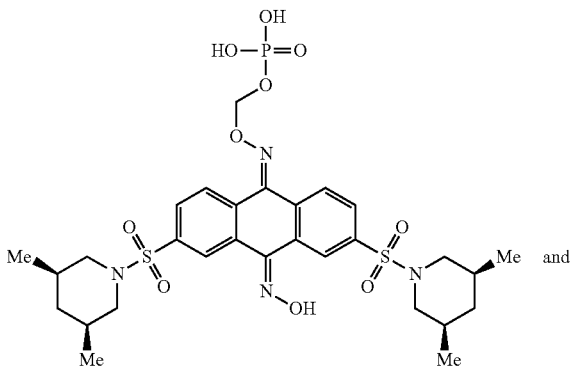

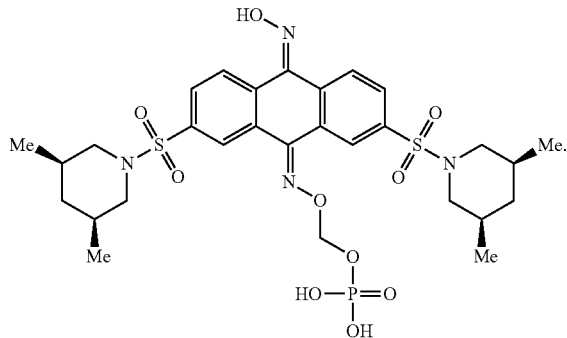

In yet another preferred embodiment, the invention provides compounds selected from the group consisting of

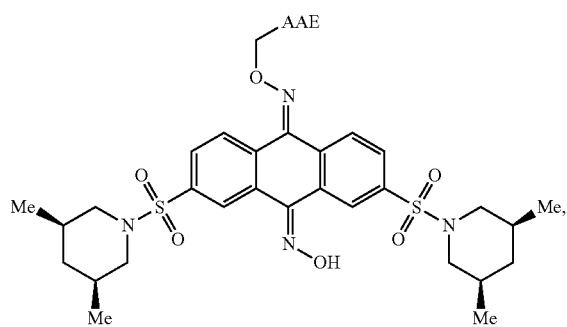

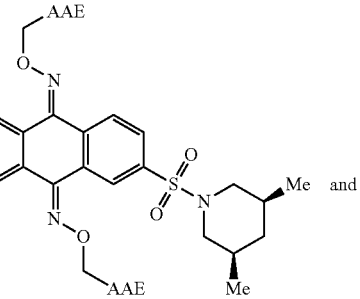

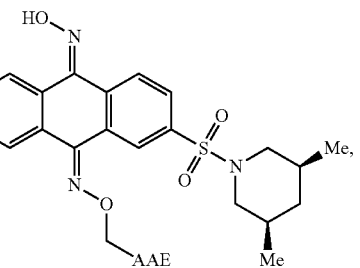

wherein AAE is an Amino Acid Ester selected from both natural and unnatural amino acids.

In yet another preferred embodiment, the invention provides compounds selected from the group consisting of

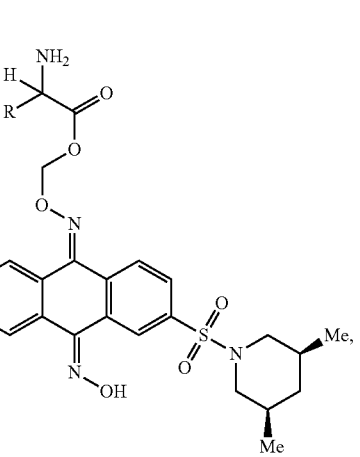

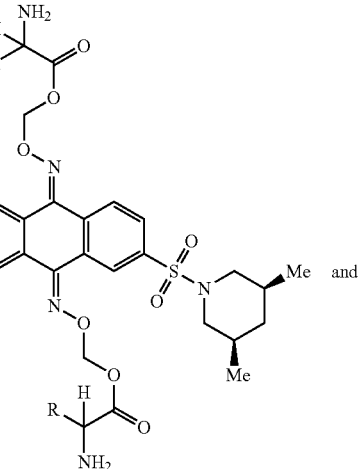

-continued

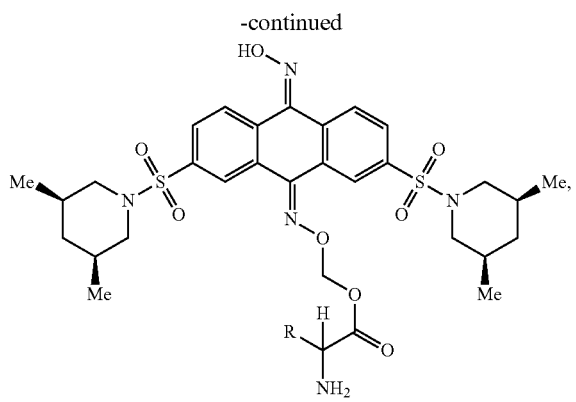

wherein R is selected from the group consisting of H, methyl, i-propyl, t-butyl, —CH₂OH, —CH₂CH(Me)₂, —CH(Me)CH₂CH₃, and

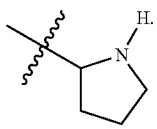

In yet another preferred embodiment, the invention provides compounds selected from the group consisting of

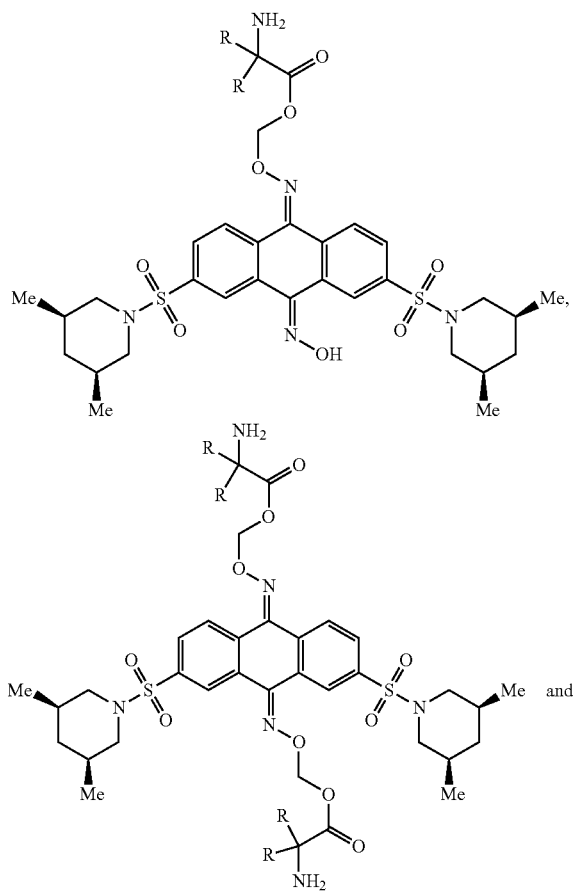

and

-continued

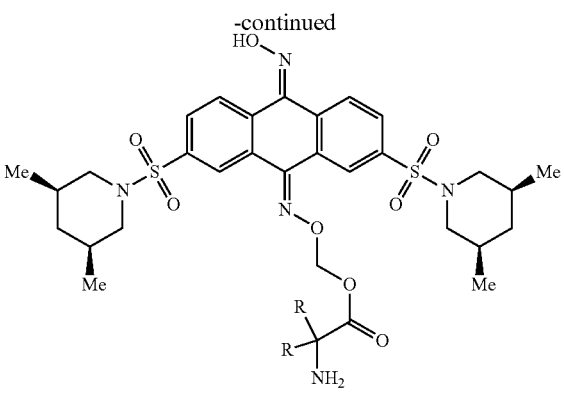

wherein R is CH₃ or ethyl, or R and R together form cyclopropyl, cyclopentyl, or pyran.

One of the preferred compounds of the invention has the following structure:

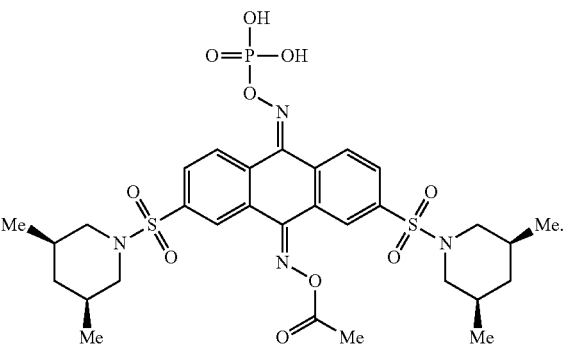 [SMILES: CC(=O)ON=C1c2cc(S(=O)(=O)N3C[C@H](C)C[C@H](C)C3)ccc2C(=NOP(=O)(O)O)c2ccc(S(=O)(=O)N3C[C@H](C)C[C@H](C)C3)cc21]

In one aspect, the present invention provides a method of preventing, treating or ameliorating cancer or tumor metastasis in a mammal in need thereof comprising administering to said mammal an effective amount of one of the compounds of the present invention.

In another aspect, the present invention provides a method for treating cancer comprising administering to a subject in need thereof a combination of: 1) a pharmaceutically effective amount of one of the compounds of the invention or a polymorph, a geometric isomer, a stereoisomer, an enantiomer, a diastereomer, a solvate, an ester, a tautomer, a metabolite or a pharmaceutically acceptable salt thereof; and 2) a pharmaceutically effective amount of at least one additional anti-cancer agent to provide a combination therapy having an enhanced therapeutic effect.

Some of the preferred additional anti-cancer agents include, but are not limited to: 1) antimitotic agents, such as taxanes (e.g., paclitaxel) or vinca alkaloids (e.g., vinblastine); 2) antimetabolite agents (e.g., fluorouracil or gemcitabine); 3) HDAC inhibitors (e.g., panobinostat); 4) proteosome inhibitors (e.g., bortezomib); 5) immunotherapeutic agents (e.g., anti-PD1, anti-PD-L1, and anti-CTLA4 antibodies); 6) FLT-3 kinase inhibitors (e.g., quizartinib); and 7) WNT pathway inhibitors (e.g., vantictumab, LGK974 or XAV939).

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

DETAILED DESCRIPTION OF THE INVENTION

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as ChemDraw™ (Cambridgesoft Corporation, U.S.A.).

Some compounds within the present invention possess one or more chiral centers, and the present invention includes each separate enantiomer of such compounds as well as mixtures of the enantiomers. Where multiple chiral centers exist in compounds of the present invention, the invention includes each possible combination of chiral centers within a compound, as well as all possible enantiomeric and diastereomeric mixtures thereof. All chiral, diastereomeric, and racemic forms of a structure are intended, unless the specific stereochemistry or isomeric form is specifically indicated. It is well known in the art how to prepare optically active forms, such as by resolution of racemic forms or by synthesis from optically active starting materials.

Specfically, any compounds described herein containing oximes or hetero-cycloalkyle group, unless specified otherwise, are meant to include both E and Z geometric isomers and R and S configurations either racemic or enentiomerically pure stereoisomers.

The term "prodrug" refers to a drug precursor compound, that undergoes transformation in vivo to yield a parent compound or a pharmaceutically acceptable salt, hydrate or solvate of the parent compound. The transformation may occur by various mechanisms by metabolic or chemical processes. A discussion of the use of prodrugs is provided by. "Prodrugs: Challenges and Rewards, Parts 1 and 2," Vol. V of the Biotechnology: Pharmaceutical Aspects (Ronald T. Borchardt and C. Russel Middaugh, series editors), ed. Valentino J. Stella, Ronald T. Borchardt, Michael J. Hageman, Reza Oliyai, Hans Maag, Jefferson W. Tilley, American Association of Pharmaceutical Scientists and Springer, 2007. Particularly favored prodrugs are those that increase the bioavailability of the parent compounds when such compounds are administered to a patient (e.g., by allowing orally administered compound to be more readily absorbed into blood) or which enhance delivery of the parent compound to a biological compartment (e.g., the brain or lymphatic system).

The compounds of the invention, which are prodrugs, may themselves have prodrugs. In that case, the term "prodrug" refers to any pharmaceutically acceptable salt, ester, salt of an ester or other derivative of a compound of this invention, which, upon administration to a recipient, is capable of providing, either directly or indirectly, a compound of this invention or a pharmaceutically active metabolite or residue thereof.

The term "metabolite" refers to any substance produced during metabolism, i.e., digestion or other bodily chemical processes.

A "pharmaceutically acceptable salt" may be prepared for any compound of the invention having a functionality capable of forming a salt, for example, an acid or base functionality. Pharmaceutically acceptable salts may be derived from organic or inorganic acids and bases. Compounds of the invention that contain one or more basic functional groups, e.g., amino or alkylamino, are capable of forming pharmaceutically acceptable salts with pharmaceutically acceptable organic and inorganic acids.

These salts can be prepared in situ during the final isolation and purification of the compounds of the invention, or by separately reacting a purified compound of the invention in its free base form with a suitable organic or inorganic acid, and isolating the salt thus formed.

Examples of suitable acid salts include, but are not limited to, acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-napthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecampate.

Other acids, such as oxalic, while not in themselves pharmaceutically acceptable, may be employed in the preparation of salts useful as intermediates in obtaining the compounds of the invention and their pharmaceutically acceptable acid addition salts. See, e.g., Berge et al. "Pharmaceutical Salts", J. Plrarrn. Sci. 1977, 66:1-19.

Compounds of the present invention that contain one or more acidic functional groups are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of some of the bases that can be used include sodium hydroxide, potassium hydroxide, choline hydroxide, sodium carbonate, N~(Cl-a alkyl)4, and the like. Representative organic amines useful for the formation of base addition salts include ethylamine, diethylamine, ethylenediamine, ethanolamine, diethanolamine, piperazine and the like. This invention also envisions the quaternization of any basic nitrogen-containing groups of the compounds disclosed herein.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of a disorder of uncontrolled cellular proliferation associated prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, zebra fish etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder of uncontrolled cellular proliferation" means having been subjected to a physical examination by a person of skill, for example, a physician, and found to have a condition that can be diagnosed or treated by a compound or composition that can inhibit uncontrolled cellular proliferation.

As used herein, the phrase "identified to be in need of treatment for a disorder," or the like, refers to selection of a subject based upon need for treatment of the disorder. For example, a subject can be identified as having a need for treatment of a disorder (e.g., a disorder related to an uncontrolled cellular proliferation) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, intraurethral administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex, and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration of a substance (e.g., a compound or a drug) that is required for 50% agonism or activation of a biological process, or component of a process, including a protein, subunit, organelle, ribonucleoprotein, etc. In one aspect, an $EC_{50}$ can refer to the concentration of a substance that is required for 50% agonism or activation in vivo, as further defined elsewhere herein. In a further aspect, $EC_{50}$ refers to the concentration of agonist or activator that provokes a response halfway between the baseline and maximum response.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. For example, an $IC_{50}$ can refer to the concentration of a substance that is required for 50% inhibition in vivo or the inhibition is measured in vitro, as further defined elsewhere herein. Alternatively, $IC_{50}$ refers to the half maximal (50%) inhibitory concentration (IC) of a substance The inhibition can be measured in a cell-line such as AN3 CA, BT-20, BT-549, HCT 116, HER218, MCF7, MDA-MB-231, MDA-MB-235, MDA-MB-435S, MDA-MB-468, PANC-1, PC-3, SK-N-MC, T-47D, and U-87 MG.

The term "pharmaceutically acceptable" describes a material that is not biologically or otherwise undesirable, i.e., without causing an unacceptable level of undesirable biological effects or interacting in a deleterious manner.

The term "stable," as used herein, refers to compounds that are not substantially altered when subjected to conditions to allow for their production, detection, and, in certain aspects, their recovery, purification, and use for one or more of the purposes disclosed herein.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "A$^1$," "A$^2$," "A$^3$," and "A$^4$" are used herein as generic symbols to represent various specific substituents. These symbols can be any substituent, not limited to those disclosed herein, and when they are defined to be certain substituents in one instance, they can, in another instance, be defined as some other substituents.

"Optionally substituted" groups may be substituted or unsubstituted. The substituents of an "optionally substituted" group may include, without limitation, one or more substituents independently selected from the following groups or designated subsets thereof: deuterium, lower alkyl, lower alkenyl, lower alkynyl, lower aryl, heteroaryl, alicyclic, heterocyclic, arylalkyl, heteroarylalkyl, lower alkoxy, lower aryloxy, amino, alkylamino, dialkylamino, diarylalkylamino, alkylthio, arylthio, heteroarylthio, oxo, oxa, carbonyl (—C(O)), carboxyesters (—C(O)OR), carboxamido (—C(O)NH$_2$), carboxy, acyloxy, —H, halo, —CN, —NO$_2$, —SH, —OH, —C(O)CH$_3$, perhaloalkyl, perhaloalkoxy, perhaloacyl, guanidine, pyridinyl, thiophene, furanyl, indole, indazole, esters, amides, phosphonates, phosphonic acid, phosphates, phosphoramides, sulfonates, sulfones, sulfates, sulphonamides, carbamates, ureas, thioureas, thioamides, thioalkyls. An optionally substituted group may be unsubstituted (e.g., —CHZCH$_3$), fully substituted (e.g., —CF$_2$CF$_3$), monosubstituted (e.g., —CHzCHzF) or substituted at a level anywhere in-between fully substituted and monosubstututed (e.g., —CHZCF$_3$).

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

For example, a "C1-C3 alkyl" group can be selected from methyl, ethyl, n-propyl, i-propyl, and cyclopropyl, or from a subset thereof. In certain aspects, the "C1-C3 alkyl" group can be optionally further substituted. As a further example, a "C1-C4 alkyl" group can be selected from methyl, ethyl, n-propyl, i-propyl, cyclopropyl, n-butyl, i-butyl, s-butyl, t-butyl, and cyclobutyl, or from a subset thereof. In certain aspects, the "C1-C4 alkyl" group can be optionally further substituted. As a further example, a "C1-C6 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, and cyclohexane, or from a subset thereof. In certain aspects, the "C1-C6 alkyl" group can be optionally further substituted. As a further example, a "C1-C8 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, cyclohexane, heptane, cycloheptane, octane, and cyclooctane, or from a subset thereof. In certain aspects, the "C1-C8 alkyl" group can be optionally further substituted. As a further example, a "C1-C12 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, cyclohexane, heptane, cycloheptane, octane, cyclooctane, nonane, cyclononane, decane, cyclodecane, undecane, cycloundecane, dodecane, and cyclododecane, or from a subset thereof. In certain aspects, the "C1-C12 alkyl" group can be optionally further substituted.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, nitrile, sulfonamide, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, nitrile, sulfonamide, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The terms "halogen," "halide," and "halo," as used herein, refer to the halogens fluorine, chlorine, bromine, and iodine. It is also contemplated that, in various aspects, halogen can be selected from fluoro, chloro, bromo, and iodo. For example, halogen can be selected from fluoro, chloro, and bromo. As a further example, halogen can be selected from fluoro and chloro. As a further example, halogen can be selected from chloro and bromo. As a further example, halogen can be selected from bromo and iodo. As a further example, halogen can be selected from chloro, bromo, and iodo. In one aspect, halogen can be fluoro. In a further aspect, halogen can be chloro. In a still further aspect, halogen is bromo. In a yet further aspect, halogen is iodo.

It is also contemplated that, in certain aspects, pseudohalogens (e.g. triflate, mesylate, tosylate, brosylate, etc.) can be used in place of halogens. For example, in certain aspects, halogen can be replaced by pseudohalogen. As a further example, pseudohalogen can be selected from triflate, mesylate, tosylate, and brosylate. In one aspect, pseudohalogen is triflate. In a further aspect, pseudohalogen is mesylate. In a further aspect, pseudohalogen is tosylate. In a further aspect, pseudohalogen is brosylate.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "BOC" as used herein is represented by the formula —C(O)—O-tBu.

The term "CBZ" as used herein is represented by the formula —C(O)—O—CH$_2$C$_6$H$_5$.

"R$_1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "ester" refers to a chemical compound derived from an acid (organic or inorganic) in which at least one —OH (hydroxyl) group is replaced by an —O-alkyl (alkoxy) group.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they differ in the three-dimensional orientations of their atoms in space. Specific stereoisomers can also be referred to as enantiomers when they are non-superimposable mirror images of one another, and a mixture of such isomers is often called an enantiomeric mixture. A 50:50 mixture of enantiomers is referred to as a racemic mixture. Diastereomers are stereoisomers which are not related to each other by a reflection. Diastereomers are not mirror images of each other.

Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

It is also appreciated that certain compounds described herein can be present as an equilibrium of geometric isomers. Geometric isomers are compounds that can exist as Z-isomer (cis) or E-isomer (trans) or a mixture of both. For example, the oxime in the following structure can exist as Z-isomer (cis) or E-isomer (trans) or a mixture of both.

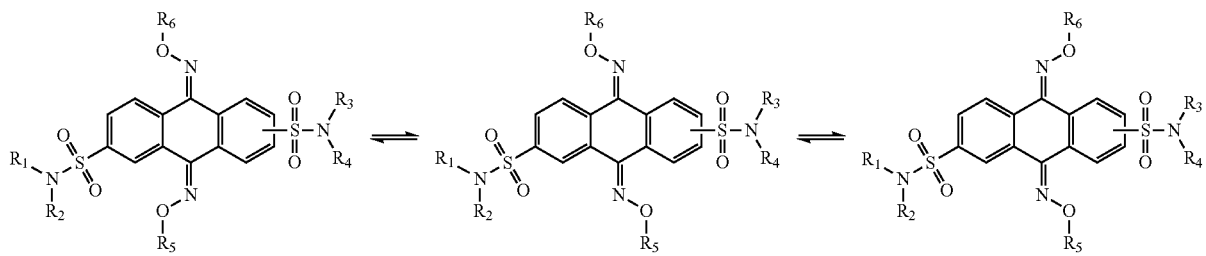

Likewise, amides with an N-hydrogen can exist in an equilibrium of the amide form and the imidic acid form. Unless stated to the contrary, the invention includes all such possible tautomers. Tautomers are constitutional isomers of organic compounds that readily interconvert by a chemical reaction called tautomerization. This reaction commonly results in the formal migration of a hydrogen atom or proton, accompanied by a switch of a single bond and adjacent double bond.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

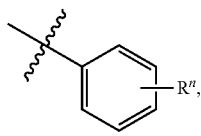

which is understood to be equivalent to a formula:

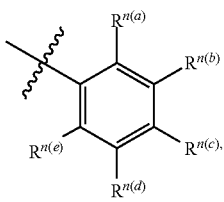

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

In some aspects, a structure of a compound can be represented by a formula:

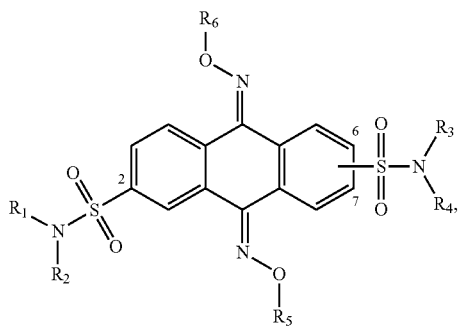

which is understood to be equivalent to a formula of 2,6- or 2,7-regioisomers:

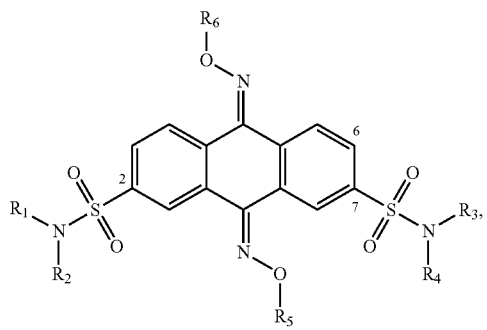

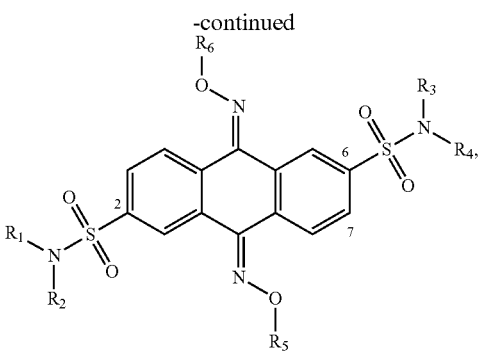

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Sigma-Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as *Fieser and Fieser's Reagents for Organic Synthesis*, Volumes 1-17 (John Wiley and Sons, 1991); *Rodd's Chemistry of Carbon Compounds*, Volumes 1-5 and Supplementals (Elsevier Science Publishers, 1989); *Organic Reactions*, Volumes 1-40 (John Wiley and Sons, 1991); March's *Advanced Organic Chemistry*, (John Wiley and Sons, 4th Edition); and Larock's *Comprehensive Organic Transformations* (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

In some aspects, the compounds of the present invention may include (that is, be attached to) an amino acid ester (AAE). AAE attached structures can be represented by a formula:

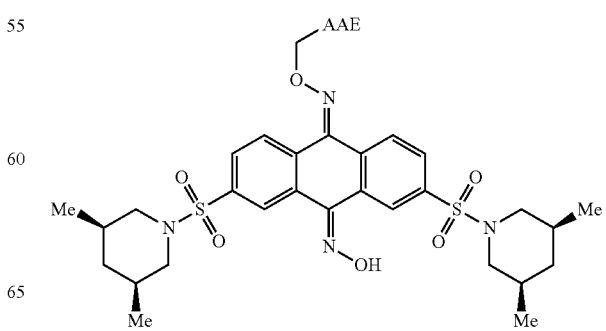

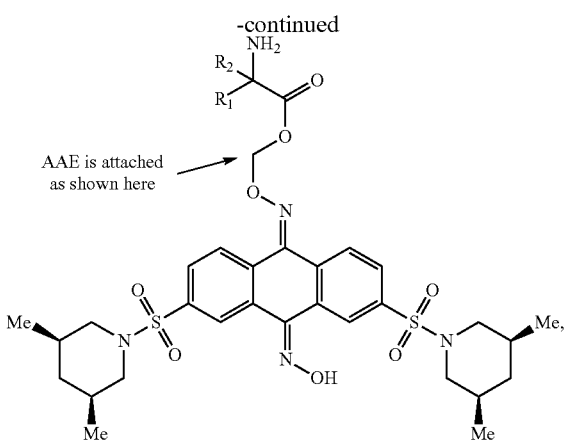

AAE is attached as shown here

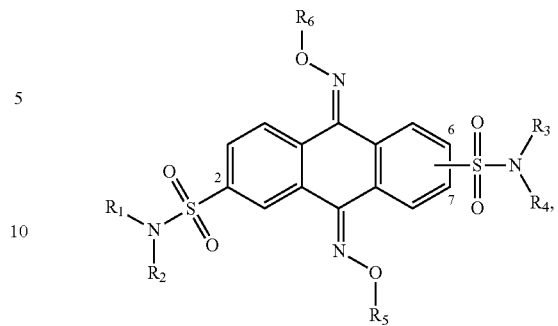

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention provides the compounds of the following formula:

wherein
$R_1$, $R_2$, $R_3$, and $R_4$ are each independently selected from H, alkyl, heteroalkyl, cycloalkyl, arylcycloalkyl, alkenyl, alkynyl, aryl, heteroaryl, heterocycloalkyl, and each of said $NR_1R_2$ and $NR_3R_4$ can independently combine to form a 6- to 15-membered heterocycloalkyl;
$R_5$ and $R_6$ are independently selected from the group consisting of H, —P(O)(OH)$_2$, —CHR$_7$—O—P(O)(OH)$_2$, —C(O)—R$_8$, and —CHR$_7$—O—C(O)—R$_8$,
$R_7$ is H or an optionally substituted lower alkyl;
$R_8$ is a lower alkyl, —OR$_{11}$, -aryl, heteroaryl or heterocycloalkyl, wherein said lower alkyl, aryl, heteroaryl or heterocycloalkyl is optionally substituted with —NR$_9$R$_{10}$ and/or OR$_{12}$;
$R_9$ and $R_{10}$ are independently selected from the group consisting of H, —P(O)(OH)$_2$, and optionally substituted lower alkyl;
$R_{11}$ is independently selected from the group consisting of lower alkyl, aryl, heteroaryl and heterocycloalkyl wherein said lower alkyl, aryl, heteroaryl or heterocycloalkyl is optionally substituted with —NR$_9$R$_{10}$ and/or —OH; and
$R_{12}$ is H or —P(O)(OH)$_2$, or
a polymorph, a geometric isomer, a stereoisomer, an enantiomer, a diastereomer, a solvate, an ester, a tautomer, a metabolite, or a pharmaceutically acceptable salt thereof.

In one preferred embodiment, the invention provides compounds wherein $NR_1R_2$ and $NR_3R_4$ are selected from

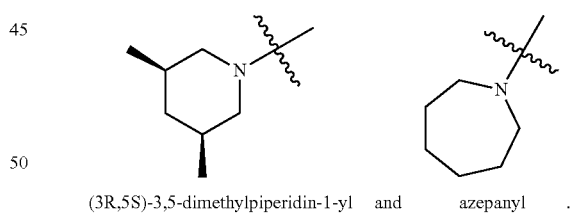

(3R,5S)-3,5-dimethylpiperidin-1-yl and azepanyl

In another preferred embodiment, the invention provides compounds wherein $R_5$ is H.

In another preferred embodiment, the invention provides compounds wherein $R_5$ and $R_6$ are independently selected from the group consisting of H, and —P(O)(OH)$_2$.

In yet another preferred embodiment, the invention provides compounds wherein $R_5$ and $R_6$ are independently selected from the group consisting of H, —P(O)(OH)$_2$, and —CHR$_7$—O—P(O)(OH)$_2$.

In yet another preferred embodiment, the invention provides compounds wherein $R_6$ is —P(O)(OH)$_2$.

In yet another preferred embodiment, the invention provides compounds wherein $NR_1R_2$ and $NR_3R_4$ are selected from

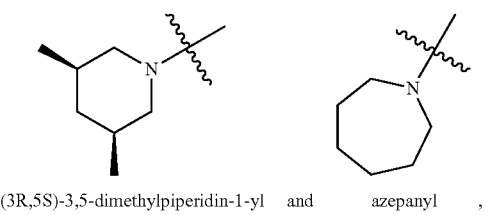

(3R,5S)-3,5-dimethylpiperidin-1-yl  and  azepanyl, and $R_5$ and $R_6$ are independently selected from the group consisting of H, —P(O)(OH)$_2$, and —CHR$_7$—O—P(O)(OH)$_2$.

In yet another preferred embodiment, the invention provides compounds wherein $R_5$ and $R_6$ are independently selected from the group consisting of H, —C(O)—R$_8$, and —CHR$_7$—O—C(O)—R$_8$.

In yet another preferred embodiment, the invention provides compounds wherein NR$_1$R$_2$ and NR$_3$R$_4$ are selected from

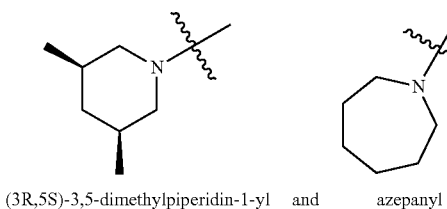

(3R,5S)-3,5-dimethylpiperidin-1-yl  and  azepanyl and wherein $R_5$ and $R_6$ are independently selected from the group consisting of H, —C(O)—R$_8$, and —CHR$_7$—O—C(O)—R$_8$.

In yet another preferred embodiment, the invention provides compounds selected from the group consisting of

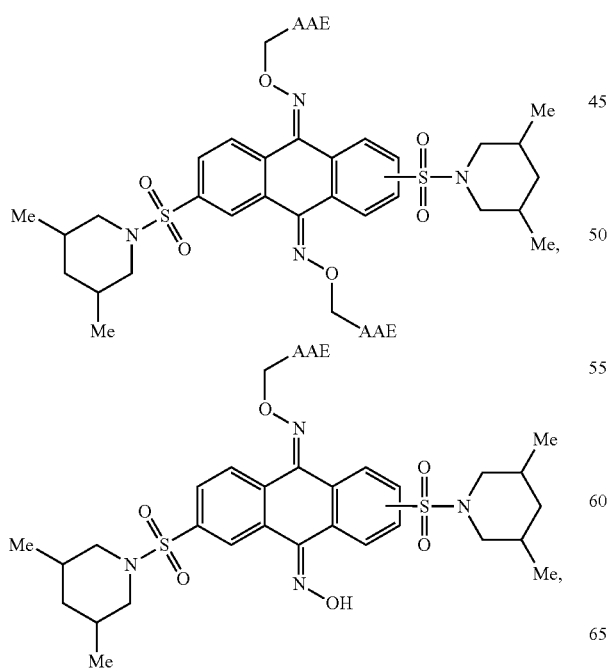

wherein AAE is an Amino Acid Ester selected from both natural and unnatural aminoacids.

In yet another preferred embodiment, the invention provides compounds selected from the group consisting of

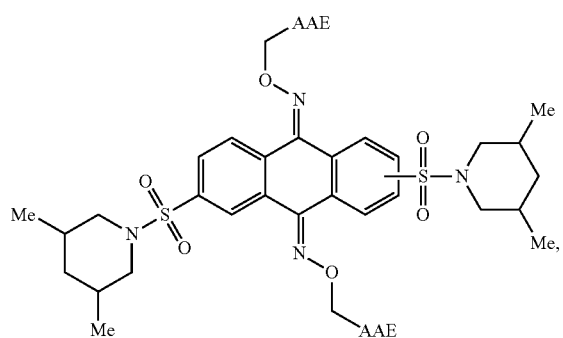
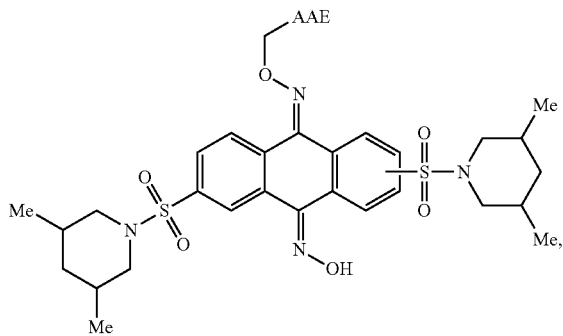
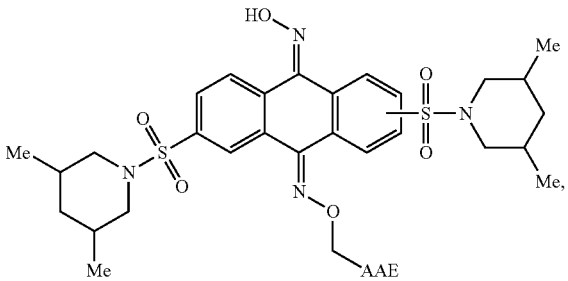
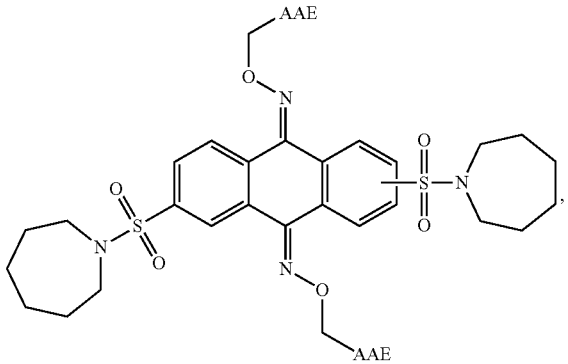
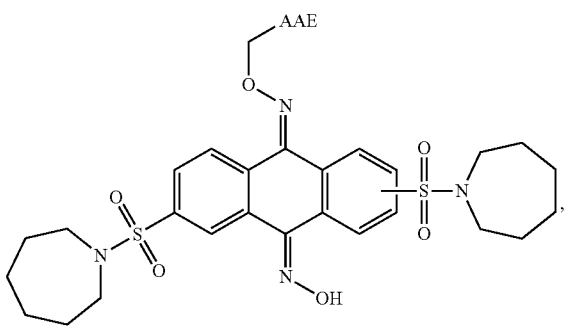
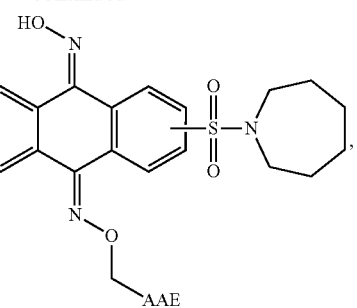
wherein AAE is selected from the group consisting of Glycine, L-Alanine, L-Valine, D-Valine, L-Serine, L-Cysteine, L-Leucine, L-Isoleucine, L-Lysine, L-Phenylalanine, L-Proline, L-Tyrosine and L-Serine.
In yet another preferred embodiment, the invention provides compounds selected from the group consisting of
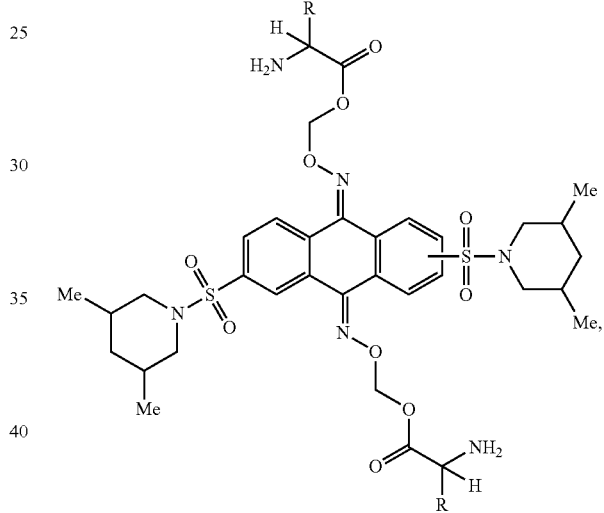
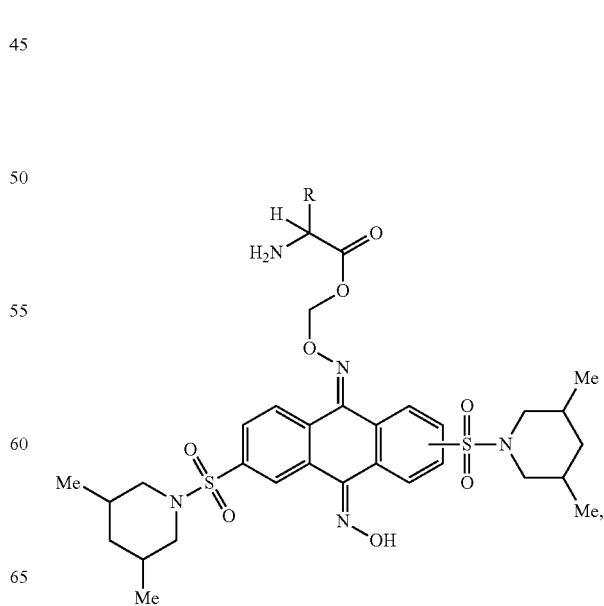

-continued

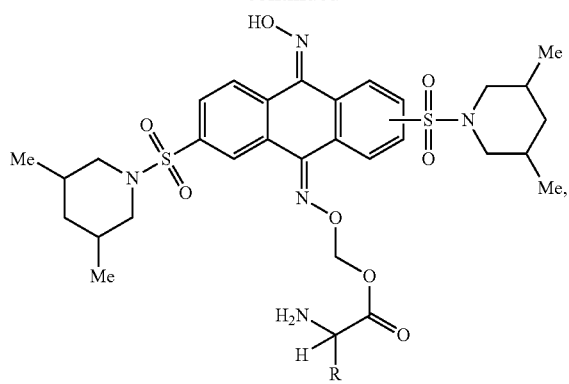

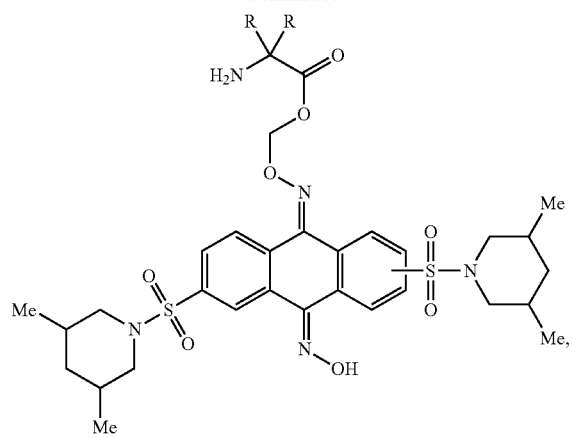

wherein R is selected from the group consisting of H, methyl, isopropyl, t-butyl, —CH₂OH, —CH₂CH(Me)₂, —CH(Me)CH₂CH, and

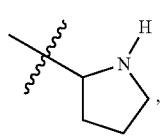

In yet another preferred embodiment, the invention provides compounds selected from the group consisting of

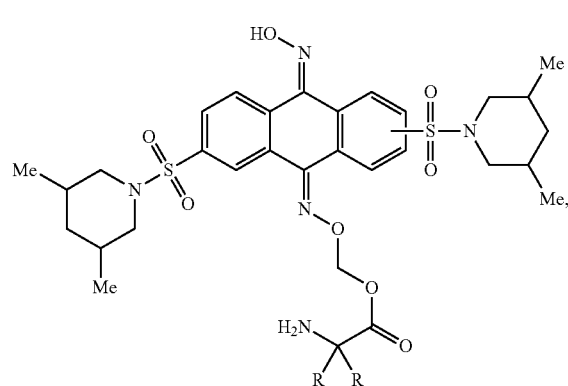

wherein R is CH₃ or ethyl, or R and R together form cyclopropyl, cyclopentyl, or pyran.

In yet another preferred embodiment, the invention provides compounds selected from the group consisting of

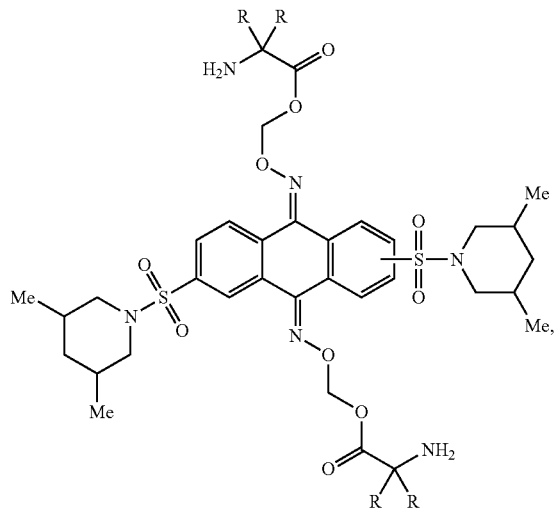

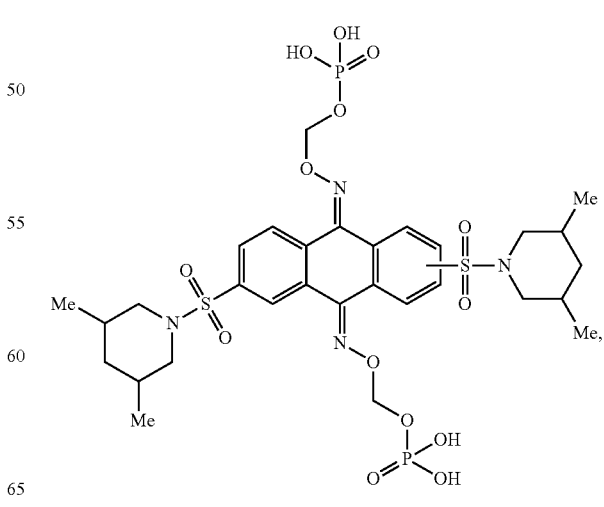

-continued
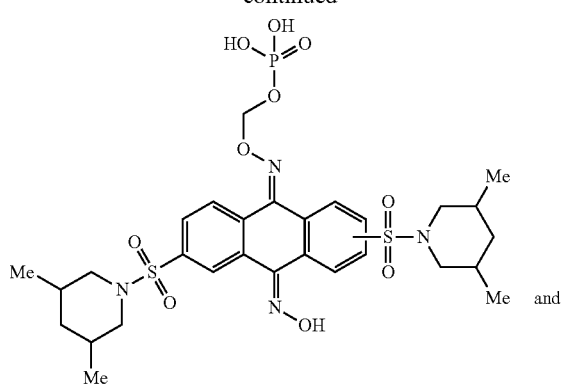
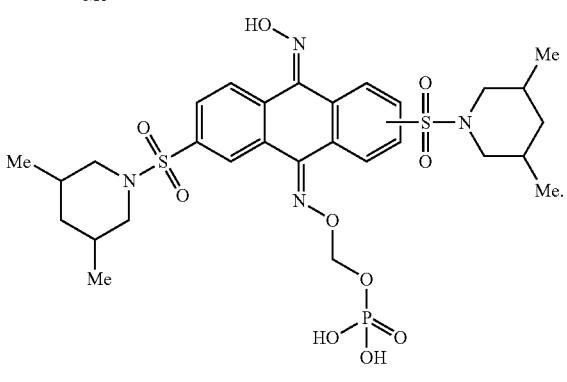
In yet another preferred embodiment, the invention provides compounds selected from the group consisting of
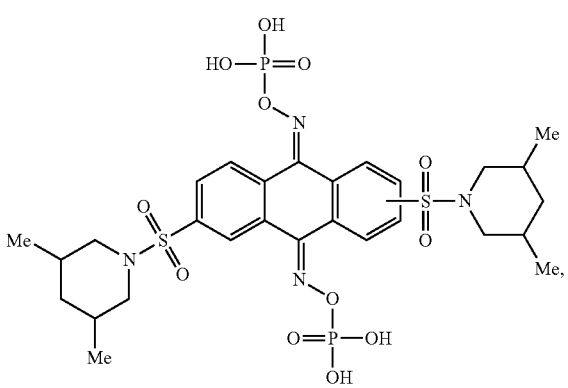
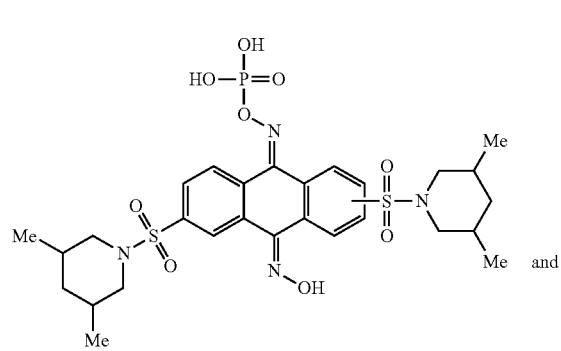 and
-continued
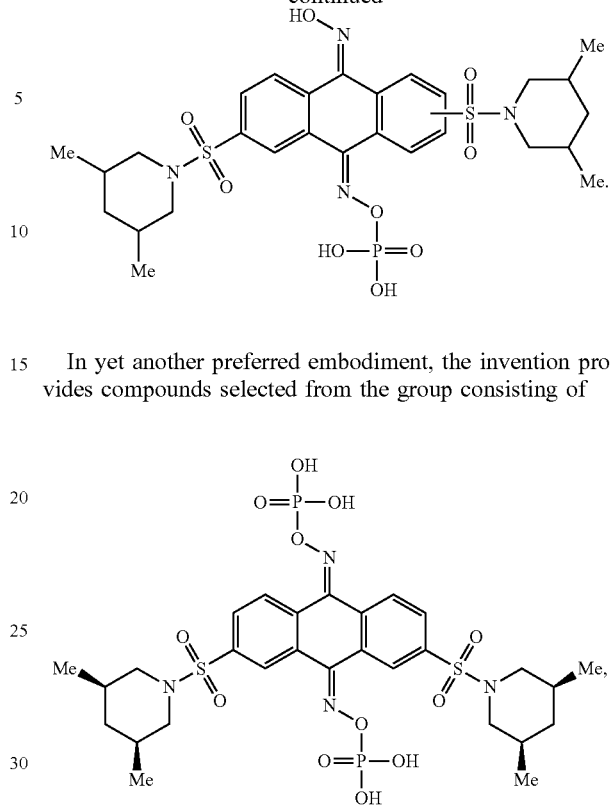
In yet another preferred embodiment, the invention provides compounds selected from the group consisting of

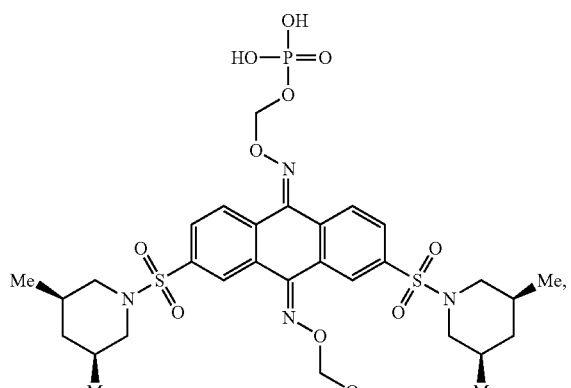
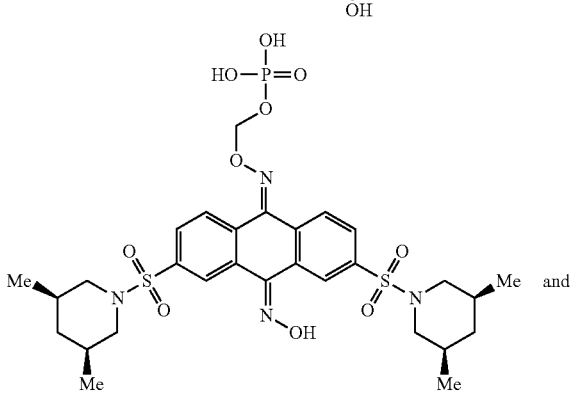
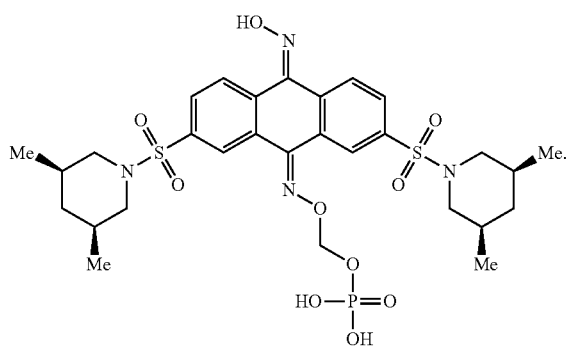
In yet another preferred embodiment, the invention provides compounds selected from the group consisting of
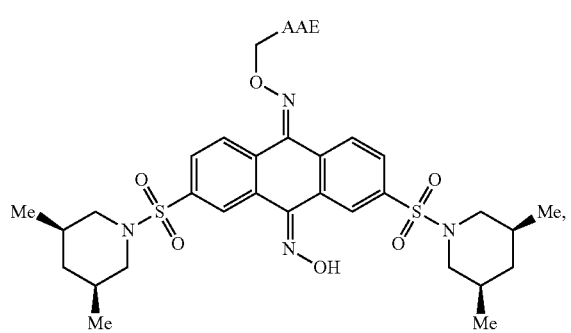
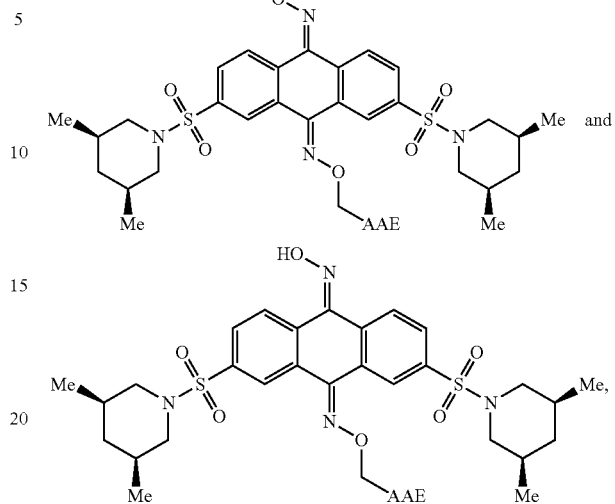
wherein AAE is an Amino Acid Ester selected from both natural and unnatural amino acids.
In yet another preferred embodiment, the invention provides compounds selected from the group consisting of
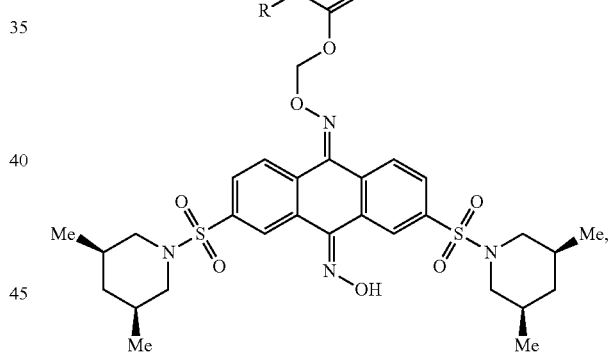
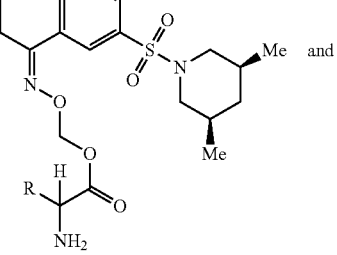

-continued

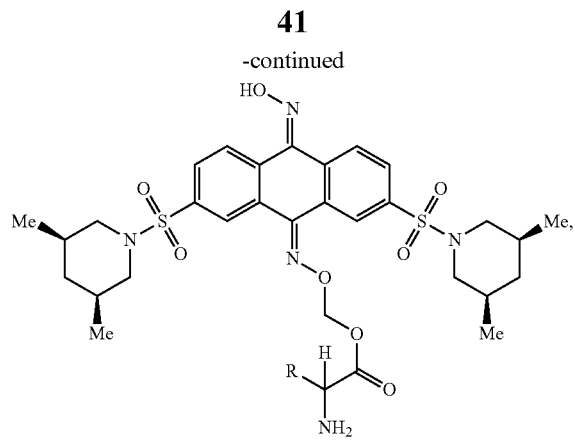

wherein R is selected from the group consisting of H, methyl, i-propyl, t-butyl, —CH₂OH, —CH₂CH(Me)₂, —CH(Me)CH₂CH₃, and

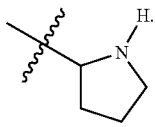

In yet another preferred embodiment, the invention provides compounds selected from the group consisting of

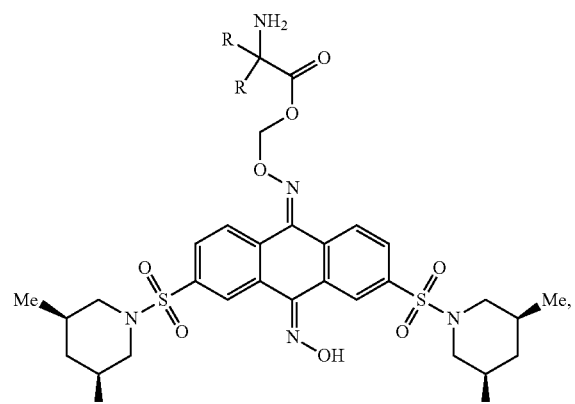

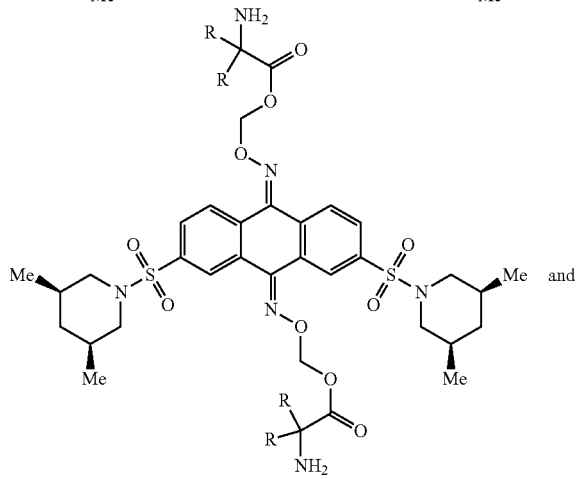

and

-continued

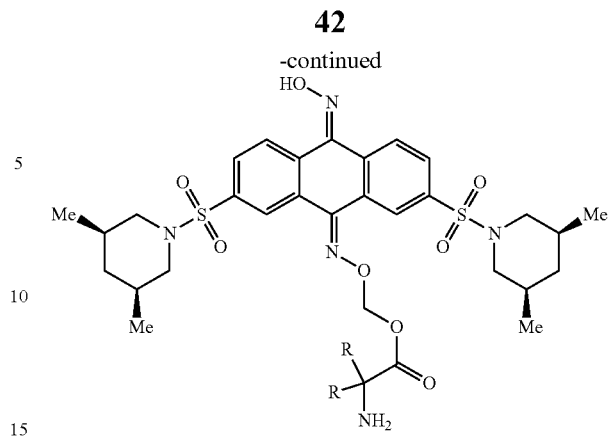

wherein R is CH₃ or ethyl, or R and R together form cyclopropyl, cyclopentyl, or pyran.

One of the preferred compounds of the invention has the following structure:

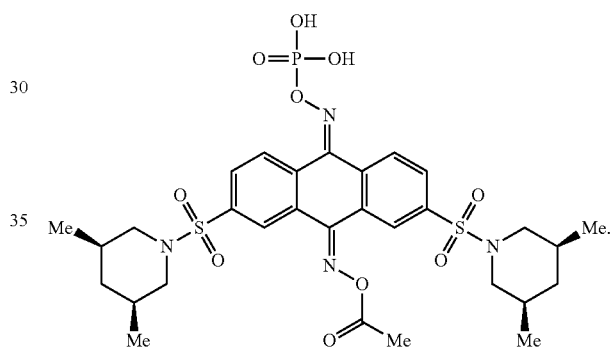

The invention also provides a pharmaceutical composition comprising a therapeutically effective amount of any of the compounds of the invention and a pharmaceutically acceptable carrier.

C. Methods of Making the Compounds

In one aspect, the invention relates to methods of making compounds of the invention.

The compounds of this invention can be prepared by employing reactions as shown in the following generic schemes by methods using various acid chlorides or anhydrides in presence of base. Alternately, the esters can be prepared using variuos acids in presence of coupling reagents like dicyclohexylcarbodiimide (DCC)/4-Dimethylaminopyridine (DMAP); hydroxybenzotriazole (HOBT)/1-Ethyl-3-(3-dimethylaminopropyl)carbodiimide (EDCI)/base or Mitsunobu esterification.

Phosphate esters can be prepared as follows:

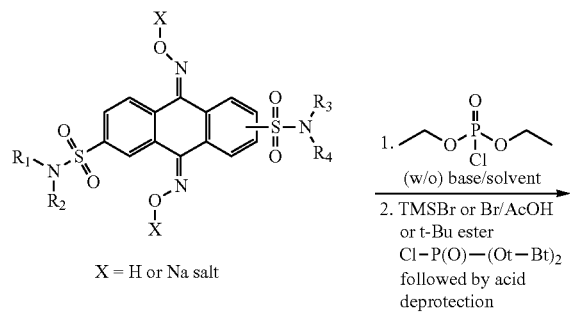

X = H or Na salt alternatively

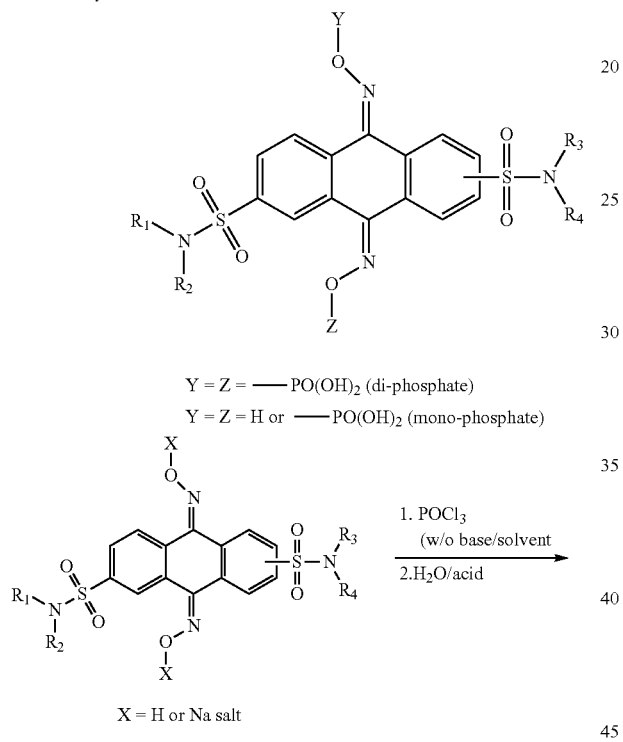

Y = Z = —PO(OH)$_2$ (di-phosphate)
Y = Z = H or —PO(OH)$_2$ (mono-phosphate)

X = H or Na salt

Y = Z = —PO(OH)$_2$ (di-phosphate)
Y = Z = H or —PO(OH)$_2$ (mono-phosphate)

the phosphate salts can be prepared using their corrosponding hydroxides, Na salt from NaOH, K salt from KOH etc.

Amino Acid Ester prodrugs can be prepared as follows:

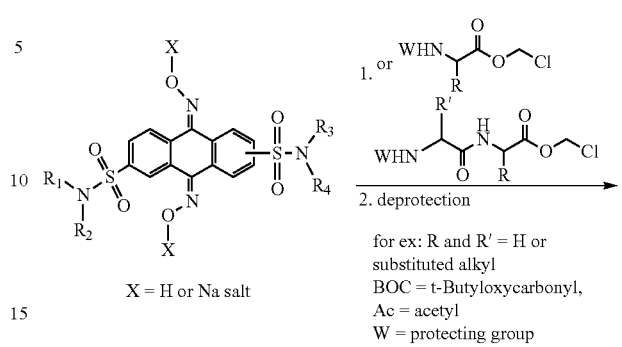

X = H or Na salt for ex: R and R' = H or substituted alkyl
BOC = t-Butyloxycarbonyl,
Ac = acetyl
W = protecting group

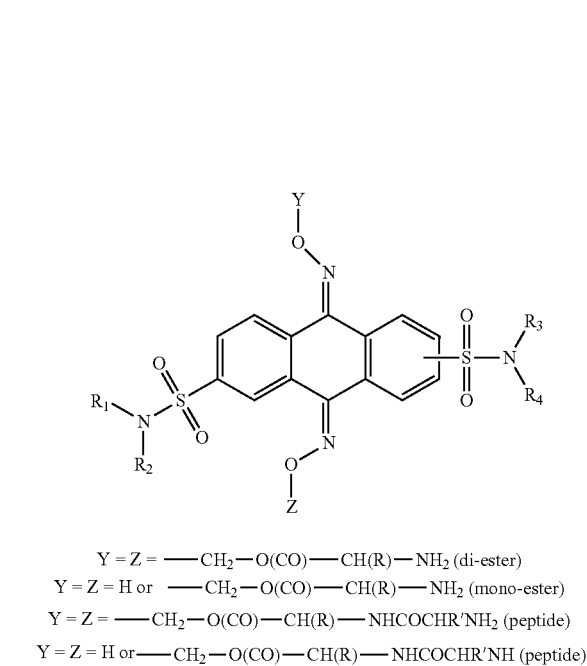

Y = Z = —CH$_2$—O(CO)—CH(R)—NH$_2$ (di-ester)
Y = Z = H or —CH$_2$—O(CO)—CH(R)—NH$_2$ (mono-ester)
Y = Z = —CH$_2$—O(CO)—CH(R)—NHCOCHR'NH$_2$ (peptide)
Y = Z = H or —CH$_2$—O(CO)—CH(R)—NHCOCHR'NH (peptide)

alternately

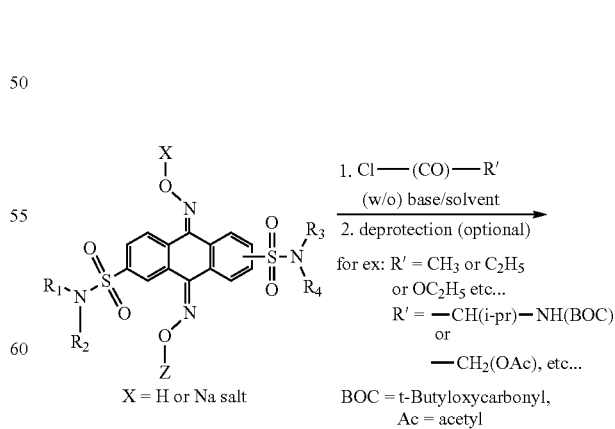

X = H or Na salt for ex: R' = CH$_3$ or C$_2$H$_5$
or OC$_2$H$_5$ etc...
R' = —CH(i-pr)—NH(BOC)
or
—CH$_2$(OAc), etc...
BOC = t-Butyloxycarbonyl,
Ac = acetyl

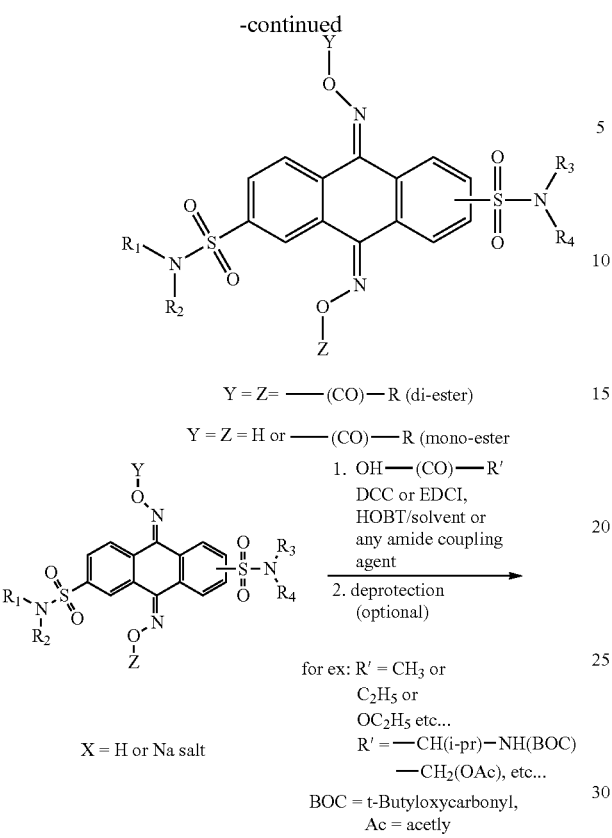

Y = Z = —(CO)—R (di-ester)

Y = Z = H or —(CO)—R (mono-ester

1. OH—(CO)—R'
DCC or EDCI,
HOBT/solvent or
any amide coupling
agent
2. deprotection
(optional)

for ex: R' = CH₃ or
C₂H₅ or
OC₂H₅ etc...
R' = —CH(i-pr)—NH(BOC)
—CH₂(OAc), etc...
BOC = t-Butyloxycarbonyl,
Ac = acetly X = H or Na salt

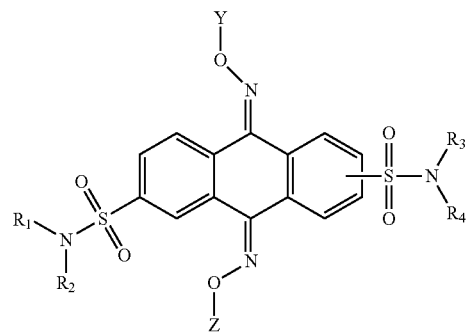

Y = Z = —(CO)—R (di-ester)

Y = Z = H or —(CO)—R (mono-ester the amine salts can be prepated using their corrosponding organic or inorganic acids, HCl, H₂SO₄, Phosphae, tartrate etc...

Less hindered mono-phosphates can be prepared as follows:

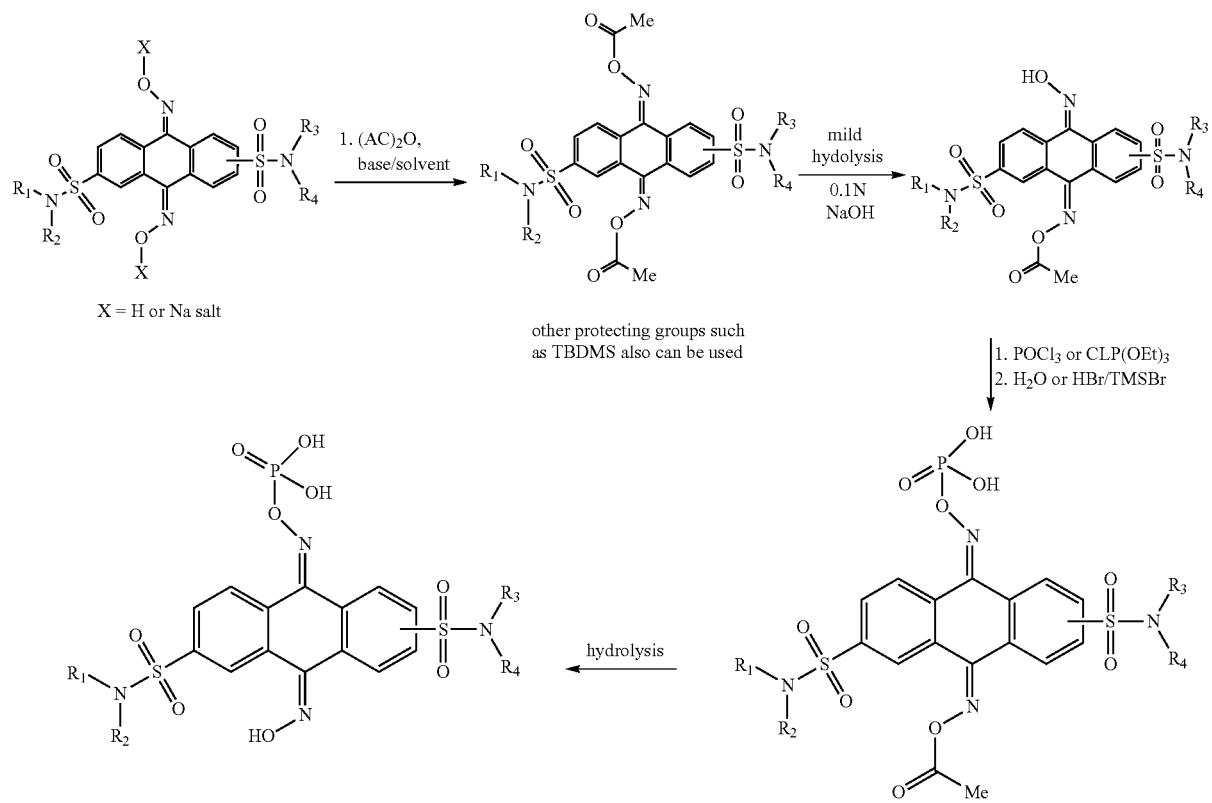

It is contemplated that each of the disclosed methods can further comprise additional steps, manipulations, and/or components. It is also contemplated that any one or more step, manipulation, and/or component can be optionally omitted from the invention. It is understood that disclosed methods can be used to provide the disclosed compounds. It is also understood that the products of the disclosed methods can be employed in the disclosed methods of using the compounds.

D. Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In a further aspect, the invention relates to pharmaceutical compositions comprising a pharmaceutically acceptable carrier and an effective amount of the product of a disclosed synthetic method. In a further aspect, the effective amount is a therapeutically effective amount. In a further aspect, the effective amount is a prophylactically effective amount. In a further aspect, the compound is a disclosed compound.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require inhibition of uncontrolled cellular proliferation, an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 miligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using the disclosed compounds.

E. Methods of Using the Compounds and Compositions

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

In accordance with the foregoing, the present invention is directed to use of the compounds of the invention as active ingredients for medicaments, in particular for medicaments useful for the treatment of tumors. The compounds of the invention will thus be present in pharmaceutical compositions containing compounds of Formula I as active ingredients, in admixture with pharmaceutically acceptable vehicles and excipients, which includes any pharmaceutical agent that does not itself induce the production of antibodies harmful to the individual receiving the composition, and which may be administered without undue toxicity. Pharmaceutically acceptable carriers include, but are not limited to, liquids such as water, saline, glycerol and ethanol, and the like, including carriers useful in forming sprays for nasal and other respiratory tract delivery or for delivery to the ophthalmic system. A thorough discussion of pharmaceutically acceptable carriers, diluents, and other excipients is presented in REMINGTON'S PHARMACEUTICAL SCIENCES (Mack Pub. Co., N.J. current edition). Use of such carriers is well known to those skilled in the art and will not be discussed further herein.

Also in accordance with the foregoing, the present invention relates to a method for preventing or treating a disease associated with a change in levels of expression of particular sets of genes in a mammal comprising administering to said mammal an effective amount of a compound of the invention.

Compounds according to the present invention will have the effect of reducing size and number of tumors, especially primary tumors, in a mammal, especially a human, in need of such treatment. A statistically significant change in the numbers of primary tumor or metastasizing cells will typically be at least about 10%, preferably 20%, 30%, 50%, 70%, 90%, or more.

In accordance with the present invention, the agents described herein may be combined with other treatments of the medical conditions described herein, such as other chemotherapies, radiation treatments, immunotherapy, surgical treatments, and the like. The compounds of the invention may also be administered in combination with such other agents as painkillers, diuretics, antidiuretics, antivirals, antibiotics, nutritional supplements, anemia therapeutics, blood clotting therapeutics, bone therapeutics, and psychiatric and psychological therapeutics.

The invention also provides a method for the treatment of a disorder of uncontrolled cellular proliferation in a mammal, the method comprising the step of administering to the mammal an effective amount of any of the compounds of the invention.

In another aspect, the present invention provides a method for treating cancer comprising administering to a subject in need thereof a combination of: 1) a pharmaceutically effective amount of one of the compounds of the invention or a polymorph, a geometric isomer, a stereoisomer, an enantiomer, a diastereomer, a solvate, an ester, a tautomer, a metabolite or a pharmaceutically acceptable salt thereof; and 2) a pharmaceutically effective amount of at least one additional anti-cancer agent to provide a combination therapy having an enhanced therapeutic effect.

Thus, in one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In one aspect, the compound can be employed in combination with anti-cancer therapeutic agents or other known therapeutic agents.

Some of the preferred additional anti-cancer therapeutic agents include, but are not limited to: 1) antimitotic agents, such as taxanes (e.g., paclitaxel) or vinca alkaloids (e.g., vinblastine); 2) antimetabolite agents (e.g., fluorouracil or gemcitabine); 3) HDAC inhibitors (e.g., panobinostat); 4) proteosome inhibitors (e.g., bortezomib); 5) immunotherapeutic agents (e.g., anti-PD1, anti-PD-L1, and anti-CTLA4 antibodies); 6) FLT-3 kinase inhibitors (e.g., quizartinib); and 7) WNT pathway inhibitors (e.g., vantictumab, LGK974 or XAV939).

Determination of the appropriate treatment dose is made by the clinician, e.g., using parameters or factors known in the art to affect treatment or predicted to affect treatment. Generally, the dose begins with an amount somewhat less than the optimum dose and it is increased by small increments thereafter until the desired or optimum effect is achieved relative to any negative side effects.

The specific dose of compound administered according to this invention to obtain therapeutic and/or prophylactic effect will, of course, be determined by the particular circumstances surrounding the case, including, for example, the specific compound administered, the route of administration, the condition being treated, and the individual being treated. A typical daily dose (administered in single or divided doses) will contain a dosage level of from about 0.01 mg/kg to about 50-100 mg/kg of body weight of an active compound of the invention. Preferred daily doses generally will be from about 0.05 mg/kg to about 25 mg/kg and ideally from about 0.1 mg/kg to about 10 mg/kg. Factors such as clearance rate, half-life and maximum tolerated dose (MTD), while not specifically recited herein, may be readily determined by one of ordinary skill in the art using standard procedures.

An effective amount of a therapeutic will modulate the symptoms typically by at least about 10%; usually by at least about 20%; preferably at least about 30%; or more preferably at least about 50%. Alternatively, modulation of migration will mean that the migration or trafficking of various cancer cell types is affected. Such will result in, e.g., statistically significant and quantifiable changes in the numbers of cells being affected. This may be a decrease in the numbers of target cells being attracted within a time period or target area. Rate of primary tumor progression, size, or growth may also be monitored.

In another aspect, the present invention relates to a method for preventing or treating a disorder modulated by altered gene expression, wherein the disorder is selected from the group consisting of cancer, cardiovascular disorders, arthritis, osteoporosis, inflammation, periodontal disorders, and skin disorders, comprising administering to a mammal in need of such treatment or prevention a therapeutically effective amount of a compound of the invention.

In a preferred embodiment, the present invention relates to a method of preventing, treating or ameliorating cancer or tumor metastasis in a mammal comprising administering to said mammal an effective a compound of the invention, preferably where said mammal is a human.

Accordingly, the pharmaceutical compositions include those that contain one or more other active ingredients, in addition to a compound of the present invention.

In the treatment of conditions which require inhibition of uncontrolled cellular proliferation, an appropriate dosage level will generally be about 0.01 to 1000 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

F. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

1. Preparation of the Compounds of the Invention

The following Examples are intended as an illustration of and not a limitation upon the scope of the onvention as defined in the appended claims.

Compounds of the invention can be made by the following experimental procedures.

Example 1

The following Scheme describes preparation of some of the compounds of the invention:

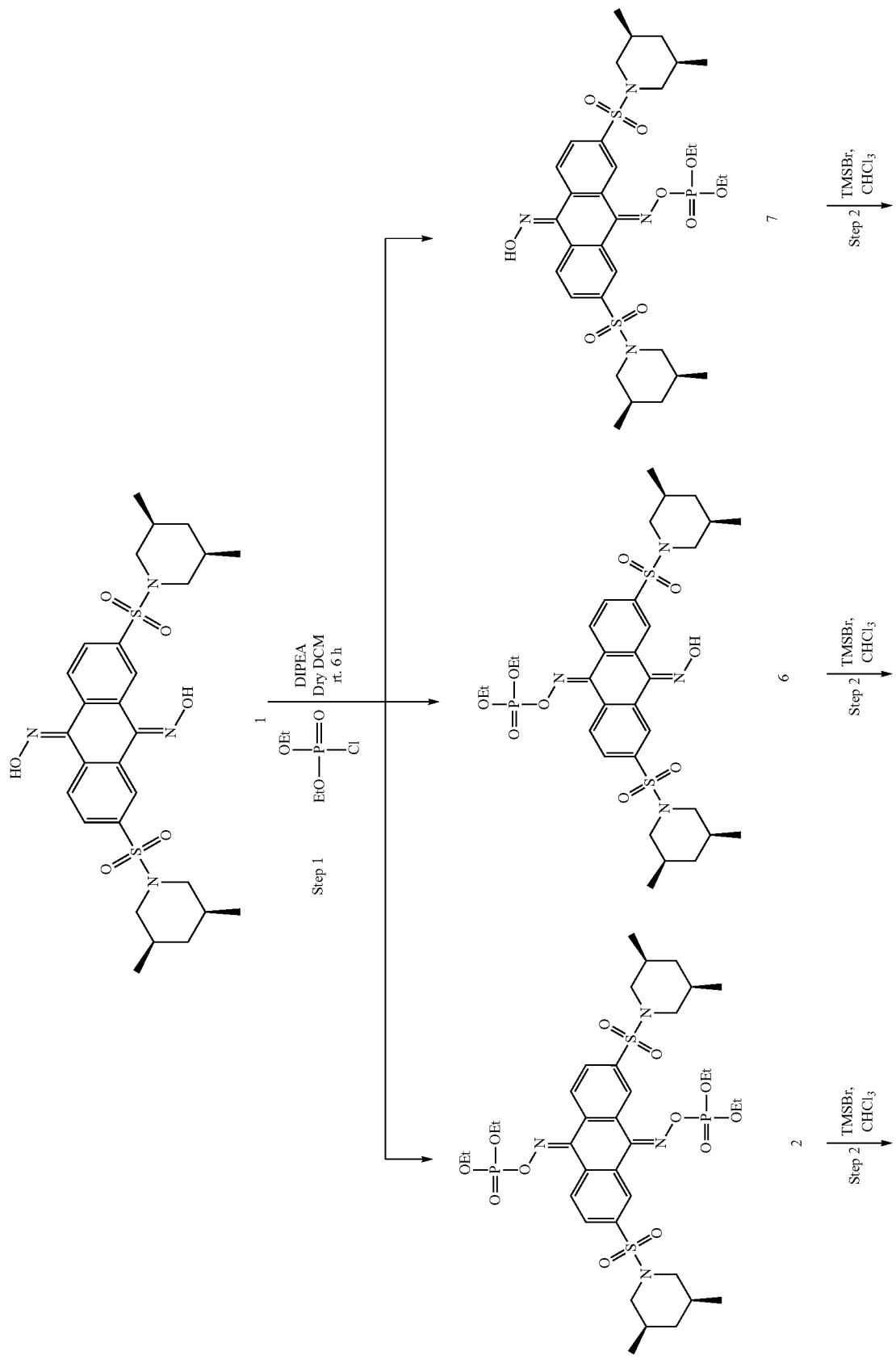

-continued
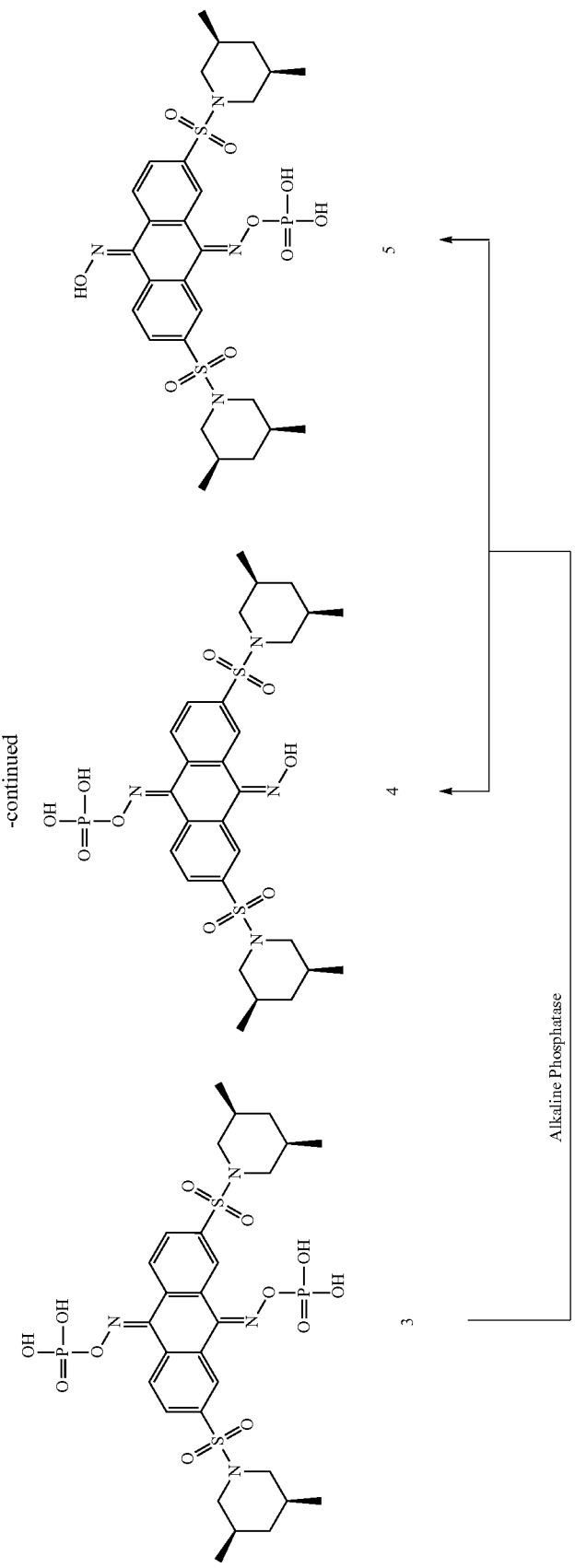

Preparation of Compounds 2, 6 and 7:

To a solution of (9E,10E)-2,7-bis(((3R,5S)-3,5-dimethylpiperidin-1-yl)sulfonyl)anthracene-9,10-dione dioxime 1 (500 mg, 0.85 mmol) in dry dichloromethane (15 mL), diisopropyl ethyl amine (164.4 mg, 1.27 mmol) was added drop wise, and the resulting mixture was stirred at room temperature for 20 min. Then, a solution of diethyl chlorophosphate (175.5 mg, 1.02 mmol) in dry dichloromethane (10 mL) was added drop wise, and the resulting mixture was stirred at room temperature for 6 h. Progress of the reaction monitored by TLC. The mixture showed 30%, 20% and 20% of compounds 2, 6 and 7 respectively with 30% remaining starting material 1. Then, the reaction mass was diluted with dichloromethane (50 mL) and washed with water (30 mL) and brine (30 mL), dried over anhydrous sodium sulfate, filtered, concentrated under reduced pressure to yield 580 mg of pale yellow solid with compounds 2, 6 and 7 in 3:2:3 ratio.

The crude compound was purified by column chromatography using 30% ethyl acetate in hexane to afford 60 mg of diethyl ((((9E,10E)-3,6-bis(((3R,5S)-3,5-dimethylpiperidin-1-yl)sulfonyl)-10-(hydroxyimino)anthracen-9(10H)-ylidene)amino)oxy)phosphonate 6 as an off white solid, 1H-NMR in CDCl3: δ 9.44 (brs, 1H), 9.09-9.05 (d, 1H), 8.65-8.58 (dd, 1H), 8.36-8.27 (d, 1H), 8.23-8.11 (dd, 1H), 7.93-7.79 (m, 2H), 4.41-4.27 (m, 4H), 3.80-3.74 (q, 4H), 1.88-1.71 (m, 10H), 1.44-1.40 (t, 6H), 0.87-0.85 (m, 12H), 0.53-0.48 (m, 2H). [M+H] calc'd for $C_{32}H_{45}N_4O_9PS_2$, 725; found 725.

Further elution with same solvent system afforded 200 mg of diethyl ((((9E,10E)-2,7-bis(((3R,5S)-3,5-dimethylpiperidin-1-yl)sulfonyl)-10-(hydroxyimino)anthracen-9(10H)-ylidene)amino)oxy) phosphonate 7 as an off white solid $R_F$: 0.4% (50% ethyl acetate in Hexane); 1H-NMR in $CDC_3$: δ 10.38-10.14 (d, 1H), 8.81-8.75 (dd, 1H), 8.36-8.32 (d, 1H), 7.91-7.85 (m, 2H), 7.82-7.79 (m, 1H), 4.47-4.37 (m, 4H), 3.77-3.73 (q 4H), 1.79-1.70 (m, 10H), 4.49-1.47 (t, 6H), 0.86-0.83 (d, 12H), 0.5-0.46 (m, 2H). [M+H] calc'd for $C_{32}H_{45}N_4O_9PS_2$, 725; found 725. HPLC: 93%.

Further elution with increased polarity 0.5% methanol in chloroform to afford 250 mg of pure tetraethyl ((((9E,10E)-2,7-bis(((3R,5S)-3,5-dimethylpiperidin-1-yl)sulfonyl)anthracene-9,10-diylidene) bis(azanylylidene))bis(oxy))bis(phosphonate) 2. 1H-NMR in $CDCl_3$) 8.87 (d, J=7.6 Hz, 1H), 8.68 (m, 1H), 8.43, 8.38 (d, J=22.4 Hz, H), 8.24 (dd, J1=8 Hz, J2=30.8 Hz, 1H), 7.94 (m, 2H), 4.36 (m, 8H), 3.77 (br-s, 4H), 1.77 (m, 8H), 1.44 (m, 12H), 0.877 (m, 12H). 31P NMR in CDCl3: δ 0.28 (d, J=10.8 Hz, 1P), 0.15 (d, J=8 Hz, 1P) EIMS: 861.28 (M+H)+.

Example 2

Synthesis of ((((9E,10E)-3,6-bis(((3R,5S)-3,5-dimethylpiperidin-1-yl)sulfonyl)-10-(hydroxyimino)-anthracen-9(10H)-ylidene)amino)oxy)phosphonic acid 4

To a solution of diethyl ((((9E,10E)-3,6-bis(((3R,5S)-3,5-dimethylpiperidin-1-yl)sulfonyl)-10-(hydroxyimino)anthracen-9(10H)-ylidene)amino)oxy)phosphonate (50 mg, 0.069 mmol) in dry chloroform (8 mL) bromotrimethyl silane (177.45 mg, 1.159 mmol) was added at 0° C., and the resulting mixture was stirred under reflux condition for 6 h. Completion of the reaction was monitored by TLC and after completion of the reaction, all the solvent was evaporated under reduced pressure and the crude residue was dissolved in 10% water in methanol (4 mL) and stirred at room temperature for 30 min. Then, methanol was evaporated under reduced pressure to dry ness and the crude solid was triturated with 5% ethyl acetate in hexane twice (2 mL×2) decanted and dried under reduced pressure to afford 40 mg (86%) of ((((9E,10E)-3,6-bis(((3R,5S)-3,5-dimethylpiperidin-1-yl)sulfonyl)-10-(hydroxyimino)-anthracen-9(10H)-ylidene)amino)oxy)phosphonic acid 4 as an off white solid. Rf: 0.1 (30% methanol in chloroform); 1H-NMR in DMSO-$d_6$: δ 13.22-13.20 (d, 1H), 9.09-9.05 (d, 1H), 8.70-8.64 (dd, 1H), 8.31-8.16 (m, 3H), 8.06-7.94 (m, 2H), 3.67-3.62 (m, 4H), 1.90-1.6 (m, 10H), 0.88-0.80 (m, 12H), 0.57-0.50 (m, 2H). [M+H] calc'd for $C_{28}H_{37}N_4O_9PS_2$; 669; found 669.

Example 3

Synthesis of (((((9E,10E)-2,7-bis(((3R,5S)-3,5-dimethylpiperidin-1-yl)sulfonyl)-10-(hydroxyimino) anthracen-9(10H)-ylidene)amino)oxy)phosphonic acid 5

Diethyl ((((9E,10E)-2,7-bis(((3R,5S)-3,5-dimethylpiperidin-1-yl)sulfonyl)-10-(hydroxyimino)anthracen-9(10H)-ylidene)amino)oxy) phosphonate 7 was hydrolyzed with TMSBr using the same procedure as in Example 2. 1H-NMR in DMSO-d6: δ 8.98-8.95 (d, 1H), 8.87-8.81 (dd, 1H), 8.31-8.22 (d, 1H), 8.18-8.09 (dd, 1H), 7.96-7.83 (m, 2H), 3.72-3.60 (m, 4H), 1.91-1.61 (m, 10H), 0.83-0.80 (m, 12H), 0.55-0.47 (m, 2H). [M+H] calc'd for $C_{28}H_{37}N_4O_9PS_2$; 669; found 669. HPLC: 99%.

Example 4

Synthesis of (((((9E,10E)-2,7-bis(((3R,5S)-3,5-dimethylpiperidin-1-yl)sulfonyl)anthracene-9,10-diylidene)-bis(azanylylidene))bis(oxy))bis(phosphonic acid) 3

Tetraethyl ((((9E,10E)-2,7-bis(((3R,5S)-3,5-dimethylpiperidin-1-yl)sulfonyl)anthracene-9, 10-diylidene) bis(azanylylidene))bis(oxy))bis(phosphonate) 2 was hydrolyzed with TMSBr using the same procedure as in Example 2. 1H-NMR in DMSO-d6: δ 8.94 (s, 1H), 8.82-8.77 (dd, H), 8.31-8.19 (m, 2H), 7.97-7.88 (m, 2H), 7.28 (brs, 4H), 3.67-3.63 (m, 4H), 1.95-1.62 (m, 10H), 0.82-0.8 (d, 12H), 0.59-0.48 (m, 2H). [M+H] calc'd for $C_{28}H_{38}N_4O_{12}P_2S_2$; 748; found 749 (M+1). HPLC: 97%.

Example 5

Alternative Synthesis for Compounds 4 and 5

Alternatively, the compounds 4 and 5 can be prepared from compound 3 using alkaline phosphatase: Compound 3 (160 mg) was dissolved into PBS buffer 75 mL with sonication for a few seconds. The almost clear solution was prewarmed to 37° C. for 10 min and 40 mL of alkaline phosphatase (Sigma A2356, 6470 units/mg, 0.08 mL, 20 mg/mL. 129 units/mL) was added. After 15 min, the solution become cloudy. The reaction was diluted with ice cold 75 ml of CH3CN after 40 min. C-18 purification gave monophosphate 4 and 5.

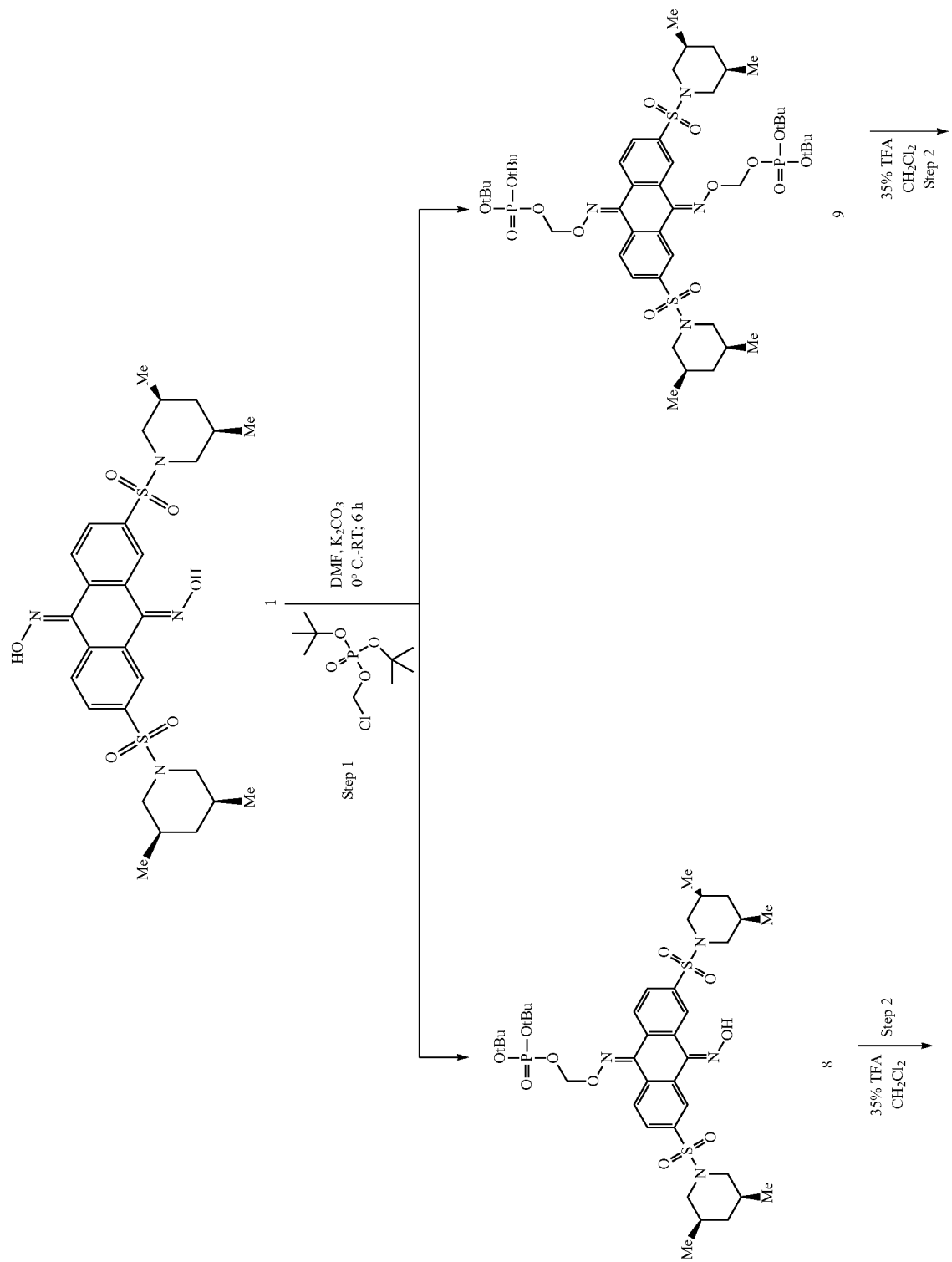

-continued
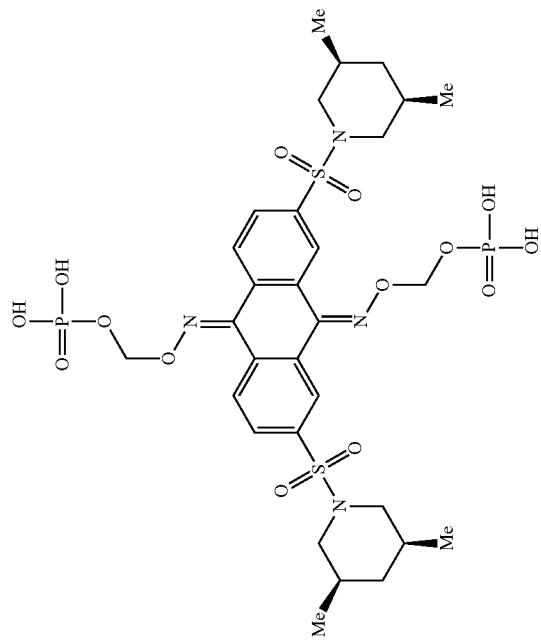
11
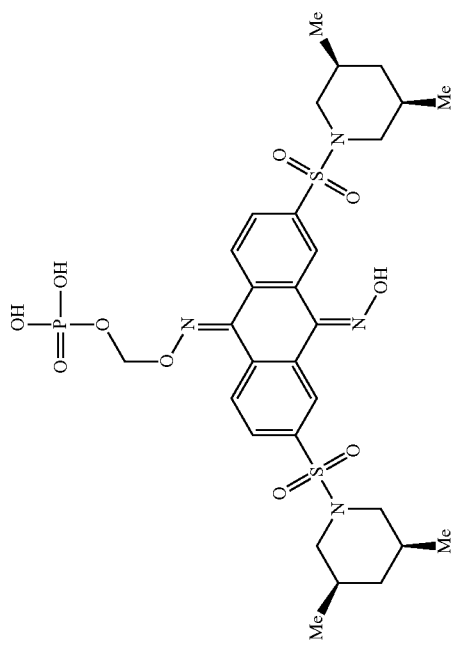
10

Example 6

Synthesis of Compounds 8 and 9

To a solution of (9E,10E)-2,7-bis(((3S,5R)-3,5-dimethyl-piperidin-1-yl)sulfonyl)-anthracene-9,10-dione dioxime (1, 1 g, 1.7 mmol) in dimethyl formamide (30 mL) potassium carbonate (352 mg, 2.5 mmol) was added and the resulting mixture was cooled to 0° C. Then a solution of Di-tert-butyl (chloromethyl) phosphate (526 mg, 2 mmol) in dimethylformamide (4 mL) was added drop wise over a period of 4 h and the resulting mixture was stirred at room temperature for 2 h. The progress of the reaction was monitored by TLC (showing~40% of the starting material remain unreacted). The reaction mass was poured in crushed ice (100 g) and extracted with ethyl acetate (40 mL×3) and the combined organic layers were washed several times with cold water (50 mL×5), and once with saturated sodium chloride solution (50 mL), dried over anhydrous sodium sulfate, filtered and concentrated under reduced pressure to afford 1.2 g of crude mixture with compounds 8:9:1 in 1:1:1.2 ratio respectively. The crude mixture was purified on neutral alumina column by eluting with chloroform to eluate the di-ester (((((9E,10E)-2,7-bis(((3S,5R)-3,5-dimethylpiperidin-1-yl)sulfonyl)anthracene-9,10-diylidene)bis (azanylylidene))bis (oxy))bis(methylene) tetra-tert-butyl bis(phosphate) 9, $R_f$=0.3; 1H-NMR in DMSO-$d_6$: δ 8.77-8.67 (m, 2H), 8.27-8.16 (m, 2H), 8.06-7.98 (m, 2H), 5.82-5.73 (m, 4H), 3.72-3.63 (m, 4H), 1.85-1.66 (m, 10H), 1.35 (s, 9H), 1.34 (s, 9H), 1.32 (s, 18H), 0.84-0.81 (m, 12H), 0.54-0.45 (m, 2H).

Further elution with ethyl acetate to produce ((((9E,10E)-3,6-bis(((3S,5R)-3,5-dimethylpiperidin-1-yl)sulfonyl)-10-(hydroxyimino)anthracen-9(10H)-ylidene)amino)oxy) methyl di-tert-butyl phosphate 8. $R_f$=0.5 (40% EtOAc/Hexane); 1H-NMR in DMSO-d6: δ 13.17-13.13 (d, 1H), 9.07-9.04 (d, 1H), 8.71-8.65 (dd, 1H), 8.29-8.13 (m, 2H), 8.00-7.89 (m, 2H), 5.82-5.78 (d, 2H), 3.67-3.62 (m, 4H), 1.85-1.62 (m, 10H), 1.314 (s, 9H), 1.309 (s, 9H), 0.83-0.79 (m, 12H), 0.51-0.48 (m, 2H).

Further elution with 15% methanol in chloroform to recover the starting material (9E,10E)-2,7-bis(((3S,5R)-3,5-dimethylpiperidin-1-yl)sulfonyl)-anthracene-9,10-dione dioxime 1.

Example 7

Synthesis of (((((9E,10E)-3,6-bis(((3S,5R)-3,5-dimethylpiperidin-1-yl)sulfonyl)-10-(hydroxyimino) anthracen-9(10H)-ylidene)amino)-oxy)methyl dihydrogen phosphate 10

To a solution of (((((9E,10E)-3,6-bis(((3S,5R)-3,5-dimethylpiperidin-1-yl)sulfonyl)-10-(hydroxyimino)anthracen-9 (10H)-ylidene)amino)oxy)methyl di-tert-butyl phosphate (100 mg) in dry dichloromethane (4 mL) 40% TFA in DCM (2.6 mL) was added at 0° C., then the resulting mixture was stirred for 1 h at room temperature Completion of the reaction was monitored by TLC. After completion of the reaction, the excess solvent and reagent was distilled under reduced pressure and the crude mixture was triturated with pentane. The resultant crude mixture (80 mg) was purified by column chromatography by eluting with 15% methanol in chloroform to afford 40 mg (46%) of ((((9E,10E)-3,6-bis (((3S,5R)-3,5-dimethylpiperidin-1-yl)sulfonyl)-10-(hydroxyimino)anthracen-9(10H)-ylidene) amino)-oxy)methyl dihydrogen phosphate as an off white solid. $R_F$=0.2 (20% MeOH in chloroform). 1H-NMR in DMSO-d6: δ 13.15-13.13 (d, 1H), 9.05-8.91 (m, 2H), 8.26-8.12 (m, 2H), 7.90-7.80 (m, 2H), 5.63-5.60 (d, 2H), 3.60-3.58 (m, 4H), 1.90-1.59 (m, 10H), 0.84-0.79 (m, 12H), 0.54-0.48 (m, 2H). [M+H] calc'd for $C_{29}H_{39}N_4O_{10}PS_2$; 698; found 699; HPLC: 97%.

Example 8

General Procedures for the synthesis of methylene bridge amino acid ester prodrugs (both natural and unnatural amino acids can be used).

The following scheme describes general synthesis procedures for the synthesis of methylene bridge amino acid ester prodrugs (both natural and unnatural amino acids can be used):

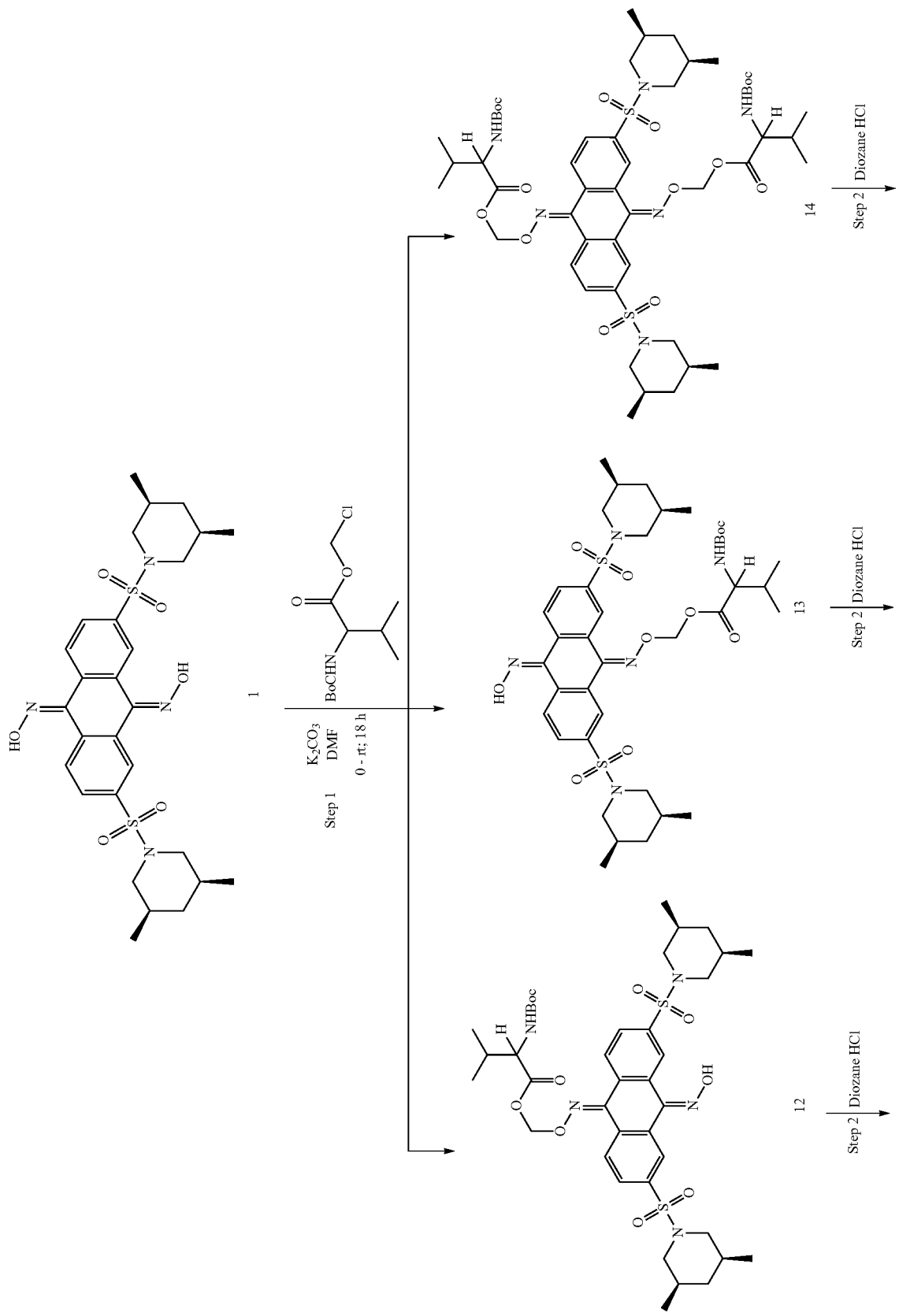

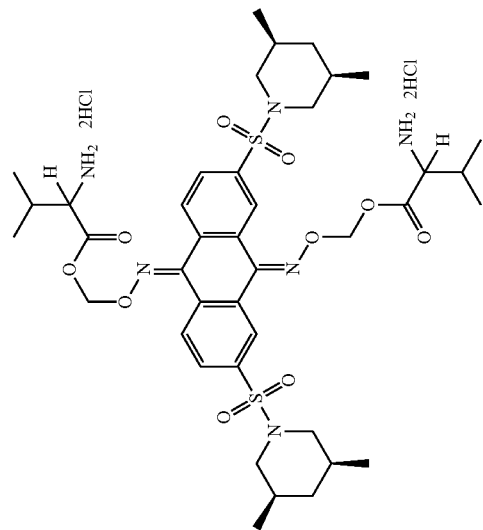
17
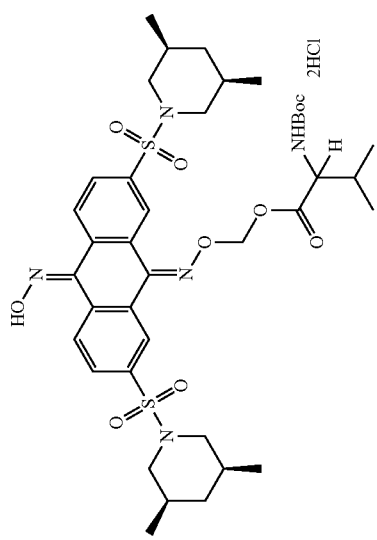
16
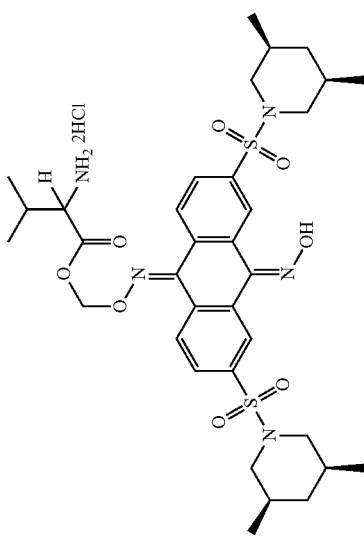
15

Example 9

Synthesis of Compounds 12, 13 and 14 (Using L-Valine)

To a suspension of sodium hydride (20 mg, 0.85 mmol) in tetrahydrofuran (40 mL), a solution of (9E,10E)-2,7-bis (((3S,5R)-3,5-dimethylpiperidin-1-yl)sulfonyl)anthracene-9,10-dione dioxime (1, 500 mg, 0.85 mmol) in tetrahydrofuran (5 mL) was added at 0° C. drop wise. The resulting solution was stirred at room temperature for 30 min, and then a solution of chloromethyl (tert-butoxycarbonyl)valinate (237 mg, 0.85 mmol; WO 2015042375) in tetrahydrofuran (5 mL) was added at 0° C. and the resulting reaction mixture was stirred for 16 h at room temperature. LCMS showed 50% completion with 2:1 ratio of upper mono 12 and lower mono 13 esters and small amount of di-alkyl product 14. The reaction mixture was neutralized with 10% citric acid solution and concentrated under reduced pressure. Then, the residue was dissolved in chloroform (150 mL) and washed with brine (50 mL), dried over anhydrous sodium sulfate, filtered and concentrated under reduced pressure to yield 500 mg of crude mixture and purified by column chromatography by eluting with 0.2% MeOH in chloroform to afford ((((9E,10E)-2,7-bis(((3S,5R)-3,5-dimethylpiperidin-1-yl)sulfonyl)anthracene-9,10-diylidene)bis(azanylylidene))bis(oxy))bis(methylene) bis(2-((tert-butoxycarbonyl)amino)-3-methylbutanoate) 14. white solid. 1H-NMR in DMSO-$d_6$. δ 8.79-8.76 (d, 1H), 8.63-8.57 (dd, 1H), 8.38-8.32 (d, 1H), 8.20-8.11 (dd, 1H), 7.95-7.84 (m, 2H), 6.06-6.02 (m, 2H), 5.99-5.87 m, 2H), 5.04-5.00 (t, 2H), 4.32-4.27 (m, 2H), 3.83-3.77 (m, 4H), 2.18-2.19 (m, 2H), 1.86-1.73 (10H), 1.42 (s, 9H), 1.40 (s, 9H), 1.31-1.24 (m, 2H), 0.97-0.95 (d, 3H), 0.92-0.83 (m, 21H), 0.54-0.49 (m, 2H).

Further elution with 0.5% MeOH in chloroform afforded ((((9E,10E)-3,6-bis(((3S,5R)-3,5-dimethylpiperidin-1-yl) sulfonyl)-10-(hydroxyimino)anthracen-9(10H)-ylidene) amino)oxy)methyl (tert-butoxycarbonyl)valinate 12. 1H-NMR in CDCl3. δ 8.83-8.75 (m, 2H), 8.38-8.31 (d, 1H), 8.15-8.06 (dd, 1H), 7.96-7.83 (m, 2H), 6.06-5.86 (dt, 2H), 5.05-5.03 (d, 1H), 4.29-4.26 (m, 1H), 3.83-3.77 (m, 4H), 2.16-2.12 (m, 1H), 1.88-1.72 (m, 10H), 1.41 (s, 9H), 0.89-0.80 (m, 18H), 0.57-0.46 (m, 2H).

Further elution with the same solvent system afforded ((((9E,10E)-2,7-bis(((3S,5R)-3,5-dimethylpiperidin-1-yl) sulfonyl)-10-(hydroxyimino)anthracen-9(10H)-ylidene) amino)oxy)methyl (tert-butoxycarbonyl)valinate 13. $R_f$=0.4 (10% EtOAc in CHCl$_3$). 1H-NMR in CDCl3. δ 8.83-8.75 (m, 2H), 8.38-8.31 (d, 1H), 8.15-8.06 (dd, 1H), 7.96-7.83 (m, 2H), 6.06-5.86 (dt, 2H), 5.05-5.03 (d, 1H), 4.29-4.26 (m, 1H), 3.83-3.77 (m, 4H), 2.16-2.12 (m, 1H), 1.88-1.72 (m, 10H), 1.41 (s, 9H), 0.89-0.80 (m, 18H), 0.57-0.46 (m, 2H).

Example 10

Synthesis of Compound 15

((((9E,10E)-3,6-bis(((3R,5S)-3,5-dimethylpiperidin-1-yl) sulfonyl)-10-(hydroxyimino)anthracen-9(10H)-ylidene) amino)oxy)methyl (tert-butoxycarbonyl)valinate, 12 (60 mg) was added to 2M dioxane HCl (1 mL) at 15° C. and stirred at room temperature for 2 h. completion of the reaction was monitored by TLC. After completion of the reaction, the excess solvent was distilled under reduced pressure and the crude compound was triturated with pentane and decanted and dried under reduced pressure to yield 30 mg (51%) of ((((9E,10E)-3,6-bis(((3S,5R)-3,5-dimethyl-piperidin-1-yl)sulfonyl)-10-(hydroxyimino)anthracen-9 (10H)-ylidene)amino)oxy)methyl valinate, 15 as hydrochloride salt. 1H-NMR in DMSO-$d_6$. δ 13.22-13.20 (d, 1H), 9.06-9.04 (d, 1H), 8.61-8.55 (dd, 1H), 8.36 (brs 2H), 8.299-8.09 (m, 2H) 7.99-7.91 (m, 2H), 6.23-6.04 (m, 2H), 4.053 (m, 1H), 3.69-3.60 (m, 4H), 2.15-2.1 (m, 1H), 1.86-1.65 (m, 10H), 0.98-0.92 (m, 1H), 0.869-0.84 (m, 6H), 0.81-0.7 (m, 12H), 0.55-0.45 (m, 2H). [M+H] calc'd for $C_{34}H_{47}N_5O_8S_2$; 718; found 718; HPLC: 94%.

Example 11

Synthesis of Compound 16

The same procedure can be followed as in Example 10. ((((9E,10E)-2,7-bis(((3S,5R)-3,5-dimethylpiperidin-1-yl) sulfonyl)-10-(hydroxyimino)anthracen-9(10H)-ylidene) amino)oxy)methyl valinate 16 hydrochloride salt as an off white solid. 1H-NMR in DMSO-$d_6$. δ 13.33-13.32 (d, 1H), 8.94-8.87 (m, 1H), 8.65-8.61 (d, 1H), 8.45 (brs, 2H), 8.25-8.14 (m, 2H), 8.05-7.92 (m, 2H), 6.2-5.93 (m, 2H), 4.09-4.01 (m, 1H), 3.67-3.62 (m, 4H), 2.15-2.05 (m, 1H), 1.80-1.65 (m, 10H), 0.93-0.80 (m, 18H), 0.54-0.49 (m, 2H). [M+H] calc'd for $C_{33}H_{45}N_5O_8S_2$; 704; found 704; HPLC: 97%.

Example 12

Synthesis of Compound 17

The same procedure can be followed as in Example 10. ((((9E,10E)-2,7-bis(((3 S,5R)-3,5-dimethylpiperidin-1-yl)sulfonyl)anthracene-9,10-diylidene)bis(azanylylidene)) bis(oxy))bis(methylene) bis(2-amino-3-methylbutanoate) 17 hydrochloride salt. 1H-NMR in CDCl3. δ 8.79-8.76 (d, 1H), 8.63-8.57 (dd, 1H), 8.38-8.32 (d, 1H), 8.20-8.11 (dd, 1H), 7.95-7.84 (m, 2H), 6.06-6.02 (m, 2H), 5.99-5.87 (m, 2H), 5.04-5.00 (t, 2H), 4.32-4.27 (m, 2H), 3.83-3.77 (m, 4H), 2.18-2.17 (m, 2H), 1.86-1.73 (m, 10H), 1.42 (s, 9H), 1.40 (s, 9H), 1.33-1.24 (m, 2H), 0.97-0.95 (d, 3H), 0.92-0.83 (m, 21H), 0.54-0.49 (m, 2H).

The following various amino acid analogs were made using the same procedure as in examples 10, 11 and 12. Listed only the regio-isomers that were isolated as pure:

((((9E,10E)-3,6-bis(((3R,5S)-3,5-dimethylpiperidin-1-yl) sulfonyl)-10-(hydroxyimino)anthracen-9(10H)-ylidene) amino)oxy)methyl 2-((tert-butoxycarbonyl)amino)-3,3-dimethylbutanoate 18. $R_f$=0.5 (10% EtOAc in chloroform). 1H-NMR:DMSO-$d_6$ δ 13.16 (brs, 1H), 9.05-9.03 (d, 1H), 8.62-8.55 (dd, 1H), 8.28-8.09 (m, 2H), 7.96-7.88 (m, 2H), 7.19-7.17 (d, 1H), 6.7-5.96 (dd, 2H), 3.82-3.80 (d, 1H), 3.67-3.62 (m, 4H), 1.82-1.65 (m, 10H), 1.28 (s, 9H), 0.82-0.81 (m, 21H), 0.50-0.47 (m, 2H). [M+H] calc'd for $C_{40}H_{57}N_5O_{10}S_2$; 832; found 832; HPLC: 97%.

((((9E,10E)-3,6-bis(((3R,5S)-3,5-dimethylpiperidin-1-yl) sulfonyl)-10-(hydroxyimino)anthracen-9(10H)-ylidene) amino)oxy)methyl 2-amino-3,3-dimethylbutanoate hydrochloride salt 19. 1H-NMR. DMSO-$d_6$: δ 13.23-13.20 (d, 1H), 9.05-9.03 (d, 1H), 8.60-8.53 (dd, 1H), 8.43 (brs, 2H), 8.29-8.08 (m, 2H), 8.0-7.91 (m, 2H), 6.23-6.03 (m, 2H), 3.87-3.84 (d, 1H), 3.7-3.6 (m, 4H), 1.8-1.64 (m, 10H), 0.86-0.80 (m, 21H), 0.511-0.48 (m, 2H). [M+H] calc'd for $C_{35}H_{49}N_5O_8S_2$; 732; found 732; HPLC: 98%.

((((9E,10E)-3,6-bis(((3R,5S)-3,5-dimethylpiperidin-1-yl) sulfonyl)-10-(hydroxyimino)anthracen-9(10H)-ylidene) amino)oxy)methyl (tert-butoxycarbonyl)leucinate 20. Yield: 17%; off white solid; 1H-NMR in DMSO-$d_6$. δ 13.2 (brs, 1H), 9.07-9.04 (d, 1H), 8.65-8.58 (dd, 1H), 8.31-8.12 (m, 2H), 7.98-7.88 (m, 2H), 7.33-7.31 (d, 1H), 6.09-5.95 (dd, 2H), 3.99-3.93 (m, 1H), 3.65-3.63 (m, 4H), 1.84-1.63 (m, 10H), 1.55-1.49 (m, 2H, 1.46-1.33 (m, 1H), 1.26 (s, 9H), 0.82-0.79 (m, 12H), 0.75-0.74 (d, 3H), 0.71-0.69 (d, 3H), 0.54-0.46 (m, 2H). [M+H] calc'd for $C_{40}H_{57}N_5O_{10}S_2$; 832; found 832; HPLC: 95%.

((((9E,10E)-3,6-bis(((3R,5S)-3,5-dimethylpiperidin-1-yl)sulfonyl)-10-(hydroxyimino)anthracen-9(10H)-ylidene) amino)oxy)methyl leucinate hydrochloride salt 21. off white color solid; 1H-NMR in DMSO-$d_6$. δ 13.22-13.20 (d, 1H), 9.08-9.04 (d, 1H), 8.64-8.56 (dd, 1H), 8.30 (bs, 2H), 8.22-8.11 (m, 2H), 8.01-7.91 (m, 2H), 6.22-6.05 (dd, 2H), 4.04-4.02 (d, 1H) 3.7-3.6 (m, 4H), 1.87-1.64 (m, 10H), 1.57-1.53 (m, 2H), 0.90-0.89 (m, 1H), 0.82-0.80 (m, 12H), 0.72-0.70 (d, 3H), 0.68-0.66 (d, 3H), 0.52-0.46 (m, 2H). [M+H] calc'd for $C_{35}H_{49}N_5O_8S_2$; 732; found 732; HPLC: 96%.

((((9E,10E)-3,6-bis(((3 S,5R)-3,5-dimethylpiperidin-1-yl)sulfonyl)-10-(hydroxyimino)anthracen-9(10H)-ylidene) amino)oxy)methyl 2-amino-2-methylpropanoate hydrochloride salt 22. white solid; 1H-NMR in DMSO-$d_6$. δ 13.24-13.21 (d, 1H), 9.08-9.04 (d, 1H), 8.76 (brs, 2H), 8.65-8.58 (m, 1H), 8.30-8.12 (m, 2H), 8.00-7.89 (m, 2H), 6.11 (s, 2H), 3.69-3.62 (m, 4H), 1.88-1.65 (m, 10H), 1.5 (s, 6H), 0.87-0.81 (m, 12H), 0.54-0.49 (m, 2H). [M+H] calc'd for $C_{33}H_{45}N_5O_8S_2$; 704; found 704; HPLC: 97%.

((((9E,10E)-3,6-bis(((3S,5R)-3,5-dimethylpiperidin-1-yl)sulfonyl)-10-(hydroxyimino)anthracen-9(10H)-ylidene) amino)oxy)methyl 2-((tert-butoxycarbonyl)amino)-3-methylpentanoate 23. pale yellow solid; NMR in DMSO-$d_6$: δ 13.17 (brs, 1H), 9.06-9.032 (d, 1H), 8.63-8.56 (dd, 1H), 8.28-8.20 (m, 2H), 7.96-7.90 (m, 2H), 7.25-7.24 (d, 1H), 6.13-5.91 (m, 2H), 3.91-3.88 (m, 1H), 3.7-3.6 (m, 4H), 1.79-1.65 (m, 10H), 0.81-0.80 (m, 14H), 0.71-0.61 (m, 6H), 0.53-0.47 (m, 21). [M+H] calc'd for $C_{40}H_{57}N_5O_{10}S_2$; M.Wt: 832; observed: 832 (M+1). HPLC: 96%

((((9E,10E)-3,6-bis(((3S,5R)-3,5-dimethylpiperidin-1-yl)sulfonyl)-10-(hydroxyimino)anthracen-9(10H)-ylidene) amino)oxy)methyl 2-amino-3-methylpentanoate hydrochloride salt 24. pale yellow solid; NMR in DMSO-$d_6$: δ 13.22-13.20 (d, 1H), 9.07-9.04 (d, 1H), 8.60-8.54 (dd, 1H), 8.44 (brs 2H), 8.29-8.22 (d, 1H), 8.20-8.09 (dd, 1H), 8.00-7.92 (m, 2H), 6.28-5.98 (m, 2H), 4.05 (m, 1H), 3.65-3.63 (m, 4H), 1.84-1.64 (m, 10H), 1.32-1.28 (m, 1H), 1.09-0.85 (m, 2H), 0.82-0.79 (m, 12H), 0.70-0.69 (m, 31), 0.64-0.63 (t, 3H), 0.51-0.46 (m, 2H). [M+H] calc'd for $C_{35}H_{49}N_5O_8S_2$; 732 observed 732 (M+1) ((((9E,10E)-3,6-bis(((3 S, 5R)-3,5-dimethylpiperidin-1-yl)sulfonyl)-10-(hydroxyimino)anthracen-9(10H)-ylidene)amino)oxy)methyl (tert-butoxycarbonyl)valinate 25. 1H-NMR in DMSO-$d_6$: δ 13.16-13.13 (d, 1H), 9.06-9.02 (d, 1H), 8.63-8.56 (dd, 1H), 8.31-8.20 (m, 2H), 7.96-7.89 (m, 2H), 7.27-7.25 (d, 1H), 6.10-5.93 (m, 2H), 3.89-3.83 (t, 1H), 3.64-3.59 (m, 4H), 1.98-1.92 (m, 1H), 1.80-1.62 (m, 10H), 1.27 (s, 9H), 0.826-0.78 (m, 18H), 0.53-0.47 (m, 2H). [M+H] calc'd for $C_{39}H_{55}N_5O_{10}S_2$; 818, observed 818 (M+1).

((((9E,10E)-2,7-bis(((3 S,5R)-3,5-dimethylpiperidin-1-yl)sulfonyl)-10-(hydroxyimino)anthracen-9(10H)-ylidene)amino)oxy)methyl (tert-butoxycarbonyl)valinate 26. 1H-NMR in DMSO-d6: δ 13.24 (brs, 1H), 8.92-8.86 (dd, 1H), 8.66-8.63 (d, 1H), 8.23-8.13 (m, 2H), 7.99-7.92 (m, 2H), 7.24-7.23 (d, 1H), 6.07-6.04 (m, 1H), 5.85-5.82 (m, 1H), 3.83-3.80 (t, 1H), 3.69-3.63 (m, 4H), 1.98-1.90 (m, 1H), 1.81-1.64 (m, 10H), 1.3 (s, 9H), 0.85-0.79 (m, 18H), 0.56-0.18 (m, 2H). [M+H] calc'd for $C_{39}H_{55}N_5O_{10}S_2$; 818, observed 816 (M−1)

((((9E,10E)-2,7-bis(((3S,5R)-3,5-dimethylpiperidin-1-yl)sulfonyl)-10-(hydroxyimino)anthracen-9(10H)-ylidene) amino)oxy)methyl valinate hydrochloride salt 27. 1H-NMR in DMSO-d6: δ 8.92-8.87 (dd, 1H), 8.67-8.64 (d, 1H), 8.23-8.13 (m, 2H), 7.99-7.92 (m, 2H), 6.07-6.04 (m, 1H), 5.85-5.83 (m, 1H), 3.69-3.63 (m, 4H), 3.20-3.19 (d, 1H), 1.82-1.62 (m, 10H), 0.85-0.80 (m, 12H), 0.56-0.55 (d, 3H), 0.54-0.52 (d, 3H), 0.52-0.45 (m, 2H). [M+H] calc'd for $C_{34}H_{47}N_5O_8S_2$; 718, observed 718 (M+1).

Synthesis of Compounds 31 and 32

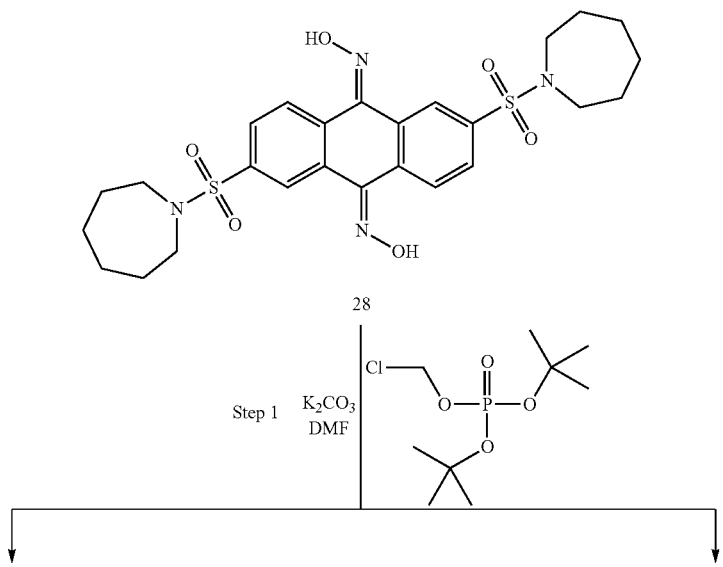

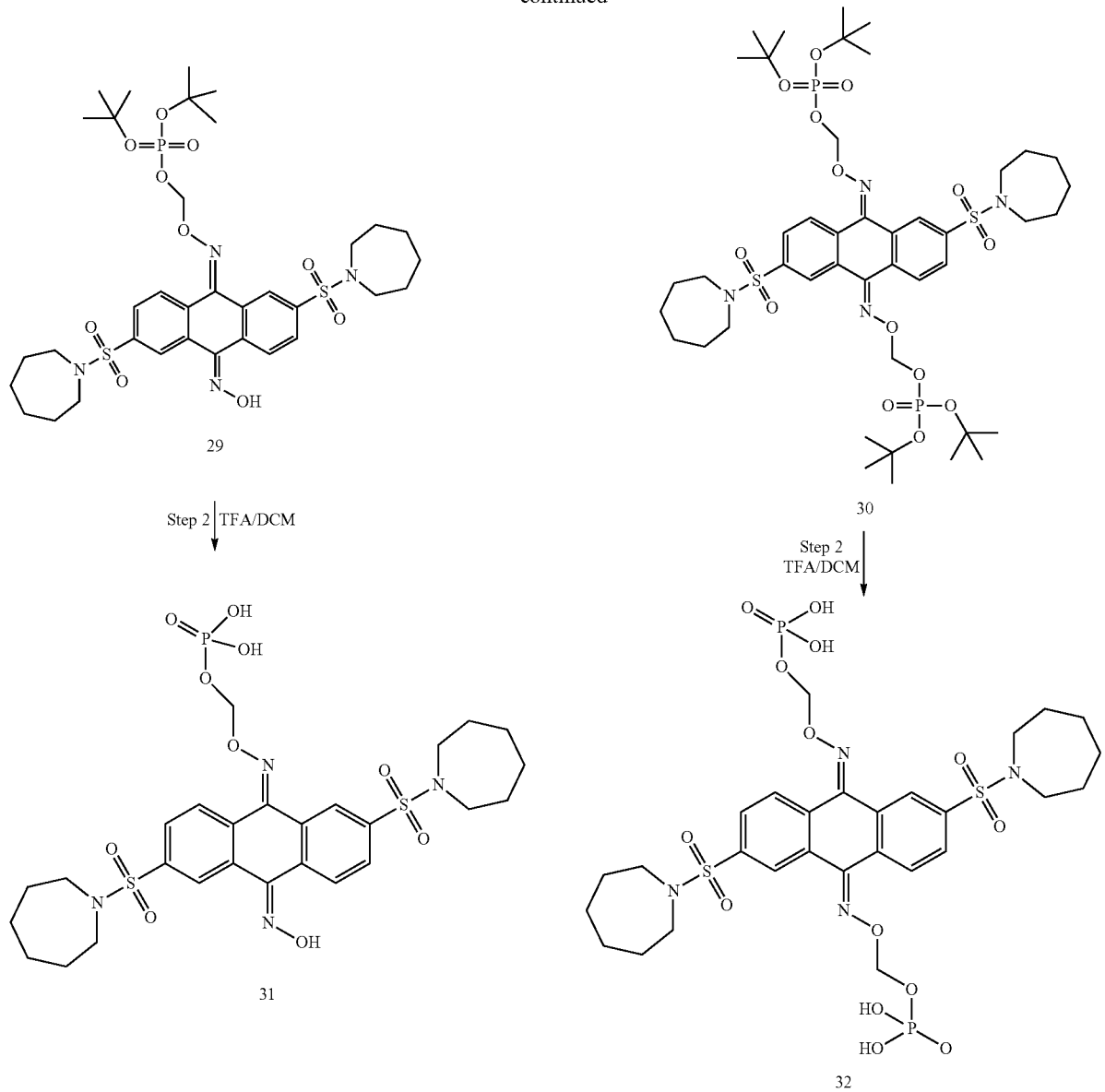

Example 13

Synthesis of Compounds 29 and 30

To a solution of ((9E,10E)-2,6-bis(azepan-1-ylsulfonyl)anthracene-9,10-dione dioxime 2 (0.5 g, 0.89 mmol) in dimethyl formamide (10 mL) potassium carbonate (197 rag, 1.4 mmol) was added and the resulting mixture was cooled to 0° C. Then a solution of Di-tert-butyl (chloromethyl) phosphate (299 mg, 1.1 mmol) in dimethylformamide (4 mL) was added drop wise over a period of 4 h and the resulting mixture was stirred at room temperature for 2 h. The progress of the reaction was monitored by TLC (showing ~20% of the starting material remain unreacted). The reaction mass was poured in crushed ice (100 g) and extracted with ethyl acetate (40 mL×3) and the combined organic layers were washed several times with cold water (50 mL×5), and once with saturated sodium chloride solution (50 mL), dried over anhydrous sodium sulfate, filtered and concentrated under reduced pressure to afford 500 mg of crude compound. The crude compound (500 mg) was purified on neutral alumina column by eluting with 0.5% methanol in chloroform to afford 110 mg (15%) of (((((9E,10E)-2,6-bis(azepan-1-ylsulfonyl)-10-(hydroxyimino)-anthracen-9(10H)-ylidene)amino)oxy)methyl di-tert-butyl phosphate 29 as an off white solid. 1H-NMR in DMSO-d6: δ 13.16-13.14 (d, 1H), 9.10-8.64 (m, 2H), 8.32-7.94 (m, 4H), 5.80-5.75 (m, 2H), 3.28-3.23 (m, 8H), 1.7-1.60 (m, 8H), 1.50-1.47 (m, 8H), 1.33 (s, 9H), 1.31 (s, 9H).

Further elusion affords 200 mg (22%) of (((((9E,10E)-2,6-bis(azepan-1-ylsulfonyl)anthracene-9,10-diylidene)-bis(azanylylidene))bis(oxy))-bis(methylene) tetra-tert-butyl bis(phosphate) 30 as an off white solid. 1H-NMR in CDCl$_3$: δ 8.91-8.89 (d, 1H), 8.77-8.68 (dd, 1H), 8.46-8.41 (d, 1H), 8.25-8.13 (dd, 1H), 7.96-7.85 (m, 2H), 5.82-5.78 (m, 4H), 3.32-3.31 (m, 8H), 1.82-1.65 (m, 8H), 1.64-1.55 (m, 8H), 1.48 (s, 18H), 1.44 (s, 18H).

Example 14

Synthesis of Compound 31

To a solution of ((((9E,10E)-2,6-bis(azepan-1-ylsulfonyl)-10-(hydroxyimino)-anthracen-9(10H)-ylidene)amino)oxy)methyl di-tert-butyl phosphate 29 (100 mg) in dry dichloromethane (10 mL) 10% TFA in dichloromethane (3 mL) was added at 0° C. and the resulting mixture was stirred for 1 h at room temperature. Completion of the reaction was monitored by TLC and after completion of the reaction, the excess solvent and reagent were distilled under reduced pressure and the rude compound was triturated with pentane and decanted and dried under reduced pressure to afford 70 mg (82%) of ((((9E,10E)-2,6-bis(azepan-1-ylsulfonyl)-10-(hydroxyimino)anthracen-9(10H)-ylidene)amino)oxy) methyl dihydrogen phosphate 31 as a white color solid. $R_f$=0.4 (40% MeOH in chloroform). 1H-NMR in DMSO-d6: δ 13.15-13.13 (d, 1H), 9.10-8.70 (m, 2H), 8.32-8.12 (m, 2H), 8.06-7.94 (m, 2H), 5.76-5.70 (m, 2H), 3.35-3.17 (m, 8H), 1.7-1.6 (m, 8H), 1.55-1.45 (m, 8H). [M+H] calc'd for $C_{27}H_{35}N_4O_{10}PS_2$; 671; found 671.

Example 15

Synthesis of Compound 32

Followed the same procedure as in Example 14, diester compound 30 yielded ((((9E,10E)-2,6-bis(azepan-1-ylsulfonyl)anthracene-9,10-diylidene)-bis(azanylylidene))bis(oxy))bis(methylene) bis(dihydrogen phosphate) 32 as a white color solid. $R_f$=0.2 (60% MeOH in chloroform). 1H-NMR in DMSO-d6: δ 8.84-8.71 (m, 2H), 8.37-8.15 (m, 2H), 8.05-7.95 (m, 2H), 5.77-5.71 (m, 4H), 3.28-3.25 (m, 8H), 1.7-1.6 (m, 8H), 1.55-1.45 (m, 8H). [M+H] calc'd for $C_{27}H_{35}N_4O_{10}PS_2$; 781; found 781.

TABLE 1

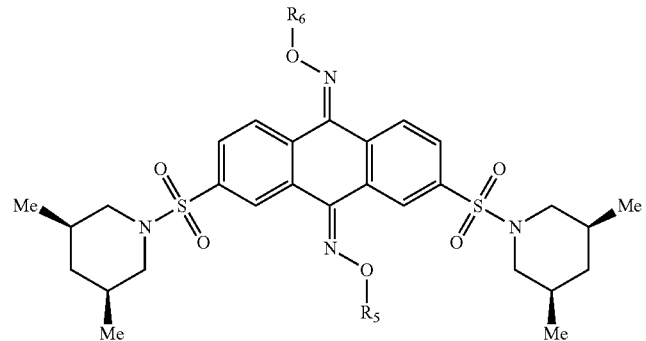

| Compound No. | $R_5$ | $R_6$ | salt |
|---|---|---|---|
| 1 | —H | —H | |
| 3 | —P(O)(OH)$_2$ | —P(O)(OH)$_2$ | Na |
| 4 | —H | —P(O)(OH)$_2$ | Na, K, tris |
| 5 | —P(O)(OH)$_2$ | —H | Na |
| 10 | —H | —CH$_2$—O—P(O)(OH)$_2$ | Na |
| 11 | —CH$_2$—O—P(O)(OH)$_2$ | —CH$_2$—O—P(O)(OH)$_2$ | Na |
| 15 | —H | —CH$_2$—O—(L-Val) | HCl |
| 16 | —CH$_2$—O—(L-Val) | —H | HCl |
| 17 | —CH$_2$—O—(L-Val) | —CH$_2$—O—(L-Val) | HCl |
| 18 | —H | —CH$_2$—O—(L-BOC-t-Bu-Leu) | HCl |
| 19 | —H | —CH$_2$—O—(L-tBu-Leu) | HCl |
| 20 | —H | —CH$_2$—O—(L-BOC-Leu) | HCl |
| 21 | —H | —CH$_2$—O—(L-Leu) | HCl |
| 22 | —H | —CH$_2$—O—C(O)—C(Me)$_2$—NH$_2$ | HCl |
| 23 | —H | —CH$_2$—O—(L-BOC-Ile) | HCl |
| 24 | —H | —CH$_2$—O—(L-Ile) | HCl |
| 25 | —H | —CH$_2$—O—(D-Val) | HCl |
| 26 | —CH$_2$—O—(D-BOC-Val) | —H | HCl |
| 27 | —CH$_2$—O—(D-Val) | —H | HCl |

TABLE 2

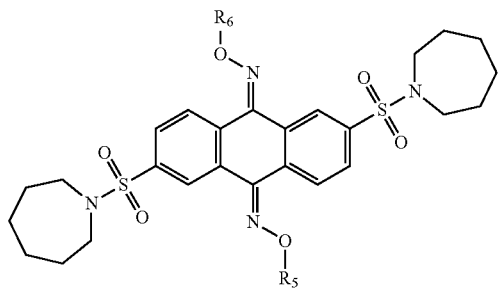

| Compound No. | $R_5$ | $R_6$ | salt |
|---|---|---|---|
| 28 | —H | —H | |
| 31 | —H | —CH$_2$—O—P(O)(OH)$_2$ | Na |
| 32 | —CH$_2$—O—P(O)(OH)$_2$ | —CH$_2$—O—P(O)(OH)$_2$ | Na |

2. Pharmacokinetic Studies of the Provided Compounds

Example 16

Pharmacokinetics of Compound 10 (Prodrug) and Estimation of Compound 1 (Parent) Following Oral and Intravenous Administration in Male Sprague Dawley Rats

| Bioanalytical method | |
|---|---|
| Study Number | 1286-16-DMPK |
| Study Type | Rat BA |
| Instrument ID | API-4000 |

| COMPOUND DETAILS: | | | | | |
|---|---|---|---|---|---|
| | Name of Compound | Molecular weight Free Form | Mol. Wt. Salt Form | Purity/potency/ assay | Diluents-Master stock preparation |
| Analyte | Compound 10 (prodrug) | 697.74 | 742.15 | 100.00% | DMSO |
| Analyte | Compound 1 (parent) | 588.20 | 588.20 | 100.00% | DMSO |
| Internal Standard | Telmisartan | 514.20 | 514.20 | 98.00% | DMSO |

| CHROMATOGRAPHY: LC Gradient: | |
|---|---|
| Mobile Phase (A) | 5 mM Ammonium Acetate |
| Mobile Phase (B) | 100% Acetonitrile |
| Column | Xbridge, C8, 4.6 × 50 mm, 5μ |
| Injection Volume (μL) | 10 |
| Flow Rate (mL/min) | 1 |
| Run Time (min) | |
| Sample Cooler Temperature (° C.) | 15 |
| Column Oven Temperature (° C.) | 40 |
| Rinsing Solution | Acetonirile:Methanol:water::20:60:20, V/V |

| SAMPLE PREPARATION: | |
|---|---|
| Extraction Technique | Protein Precipitation |
| Extraction Solvent | Acetonitrile Containing IS |

Calibration Curve & OC preparation: 2.0 μL of calibration curve standards added to 48 μL of blank matrix and precipitated with 200 μL of Acetonitrile containing internal standard at 200 ng/mL conc. then Vortexed for 5 min at 850 rpm, centrifuged at 4000 rpm for 5 min at 4° C., from this 110 μL of supernatant was separated and diluted with 130 μL of methanol:water (1:1, v/v)

Sample Preparation: 50 μL of sample was taken and precipitated with 200 μL of Acetonitrile containing internal standard at 200 ng/mL conc. then Vortexed for 5 min at 850 rpm, centrifuged at 4000 rpm for 5 min at 4° C., from this 110 μL of supernatant was separated and diluted with 130 μL of methanol:water (1:1, v/v).

| MASS SPECTROMETRIC CONDITION: | |
|---|---|
| Ionization Mode-Polarity | ESI-Negative |

| | Name of Compound | Retention Time (Min) | MRM Transitions Q1-mass | MRM Transitions Q3-mass | Declustering Potential (DP) | Entrance Potential (EP) | Collision Energy (CE) |
|---|---|---|---|---|---|---|---|
| Analyte | Compound 10 | 1.52 | 697.30 | 78.90 | −100 | −10 | −75.0 |
| Analyte | Compound 1 | 1.80 | 587.20 | 293.00 | −100 | −10 | −60.0 |
| Internal Standard | Telmisartan | 1.39 | 513.20 | 287.00 | −100 | −10 | −45.0 |

| | |
|---|---|
| Collision Cell Exit Potential (CXP) | 12 |
| Collision Gas (CAD) | 12 |
| Curtain Gas (CUR) | 30 |
| Nebulizer Gas (GS1) | 50 |
| Heater Gas (GS2) | 55 |

| | | |
|---|---|---|
| Ion spray Voltage (V) | | 5500 |
| Temperature (TEM) | | 550 |
| Interface Heater (ihe) | | off |
| Study Details | | |
| Study Number | 1286-16-DMPK | |
| Test Article Name (IV & PO) | Sodium salt of compound 10 | |
| Formulation IV solution | PEG:ethanol:water 40:10:50 | |
| Formulation PO solution | Tween 80 (0.1%) + 0.5% Methycellulose (99.9%) | |
| Species | Male Sprague Dawley Rats | |
| Study Design | Pharmacokinetic Study | |
| Matrix | Plasma | |
| Bioanalytical Details | | |
| Analyte | Sodium salt of compound 10 | |
| LLOQ | 5.01 ng/mL | ULOQ | 5001.65 ng/mL |
| Analyte | Compound 1 | |
| LLOQ | 4.0 ng/mL | ULOQ | 4000.0 ng/mL |

TABLE 3

IV PK parameters of the mean concentration data

| Parameters | Compound 10 (IV-1.28 mg/kg) Prodrug | Compound 1 (IV-1.28 mg/kg) Parent |
|---|---|---|
| Co(ng/mL) | 11437.00 | 116.31 |
| $t_{1/2}$ (h) | 1.59 | 4.00 |
| Vdss(L/ks) | 0.39 | 15.04 |
| Vd (L/kg) | 3.31 | 16.85 |
| Cl (mL/min/kg) | 24.13 | 48.34 |
| $AUC_{0-last}$ (ng · h/mL) | 868.76 | 395.85 |
| $AUC_{0-inf}$ (ng · h/mL) | 884.68 | 445.77 |
| $AUC_{Extra}$(%) | 1.81 | 11.19 |
| $MRT_{0-last}$ (h) | 0.15 | 3.56 |
| Rsq | 0.90 | 0.98 |

TABLE 4

PO PK parameters of the mean concentration data

| Parameters | Compound 10 (PO-7.46 mg/kg) Prodrug | Compound 1 (PO-7.46 mg/kg) Parent |
|---|---|---|
| Cmax (ng/mL) | — | 182.82 |
| $t_{1/2}$ (h) | — | 4.27 |
| Tmax (h) | — | 2.67 |
| $AUC_{0-last}$ (ng · h/mL) | — | 1349.94 |
| $AUC_{0-inf}$ (ng · h/mL) | — | 1383.29 |
| $AUC_{Extra}$(%) | — | 2.41 |
| $MRT_{0-last}$ (h) | — | 6.47 |
| Rsq | — | 0.9889 |
| Bioavailability (%) | — | 53.24 |

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula (I)

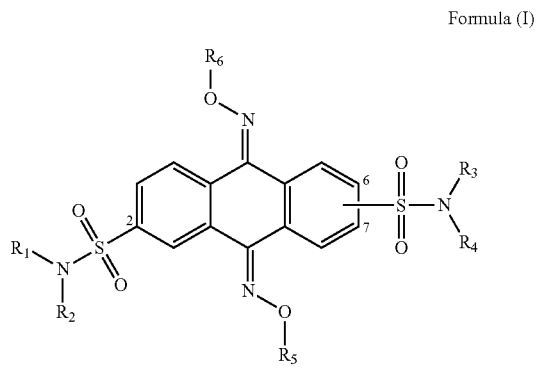

Formula (I)

or a geometric isomer, a stereoisomer, an enantiomer, a diastereomer, an ester, a tautomer, or a pharmaceutically acceptable salt thereof:

wherein $R_1$, $R_2$, $R_3$, and $R_4$ are each independently selected from H, alkyl, heteroalkyl, cycloalkyl, arylcycloalkyl, alkenyl, alkynyl, aryl, heteroaryl, heterocycloalkyl, and each of said $NR_1R_2$ and $NR_3R_4$ can independently combine to form a 6- to 15-membered heterocycloalkyl;

$R_5$ is selected from the group consisting of H, —P(O)(OH)$_2$, —CHR$_7$—O—P(O)(OH)$_2$, —C(O)—R$_8$, and —CHR$_7$—O—C(O)—R$_8$, $R_6$ is selected from the group consisting of —P(O)(OH)$_2$; CHR$_7$—O—P(O)(OH)$_2$, —C(O)—R$_8$, and —CHR$_7$—O—C(O)—R$_8$, $R_7$ is H or an optionally substituted lower alkyl;

$R_8$ is a lower alkyl, -aryl, heteroaryl or heterocycloalkyl, wherein said lower alkyl, aryl, heteroaryl or heterocycloalkyl is optionally substituted with —NR$_9$R$_{10}$ and/or OR$_{12}$;

$R_9$ and $R_{10}$ are independently selected from the group consisting of H, —P(O)(OH)$_2$, and optionally substituted lower alkyl;

$R_{11}$ is independently selected from the group consisting of lower alkyl, aryl, heteroaryl and heterocycloalkyl wherein said lower alkyl, aryl, heteroaryl or heterocycloalkyl is optionally substituted with —NR$_9$R$_{10}$ and/or —OH; and $R_{12}$ is H or —P(O)(OH)$_2$.

2. The compound of claim 1, wherein NR$_1$R$_2$ and NR$_3$R$_4$ are selected from.

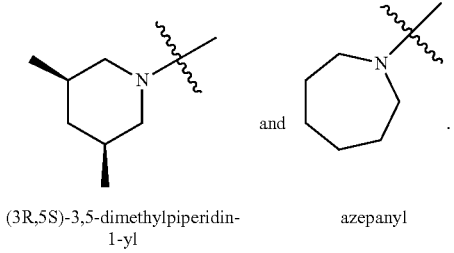

(3R,5S)-3,5-dimethylpiperidin-1-yl          azepanyl

3. The compound of claim 1, wherein R$_5$ is H.

4. The compound of claim 1, wherein R$_6$ is —P(O)(OH)$_2$.

5. The compound of claim 1, wherein R$_5$ is selected from the group consisting of H, —P(O)(OH)$_2$, and —CHR$_7$—O—P(O)(OH)$_2$; and R$_6$ is selected from the group consisting of —P(O)(OH)$_2$, and —CHR$_7$—O—P(O)(OH)$_2$.

6. The compound of claim 1, wherein R$_5$ is selected from the group consisting of H, —C(O)—R$_8$, and —CHR$_7$—O—C(O)—R$_8$; and R$_6$ is selected from the group consisting of —C(O)—R$_8$, and —CHR$_7$—O—C(O)—R$_8$.

7. A compound selected from the group consisting of

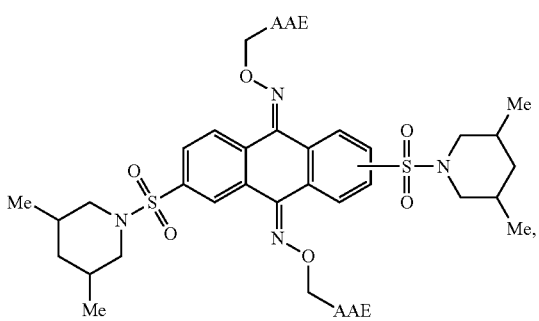

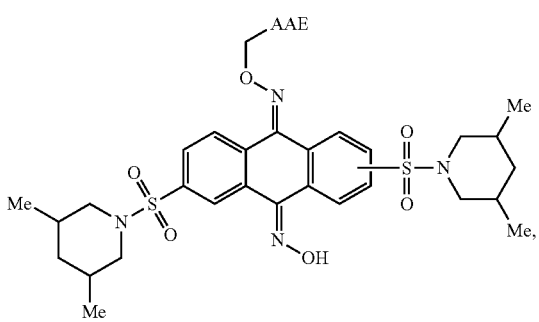

-continued

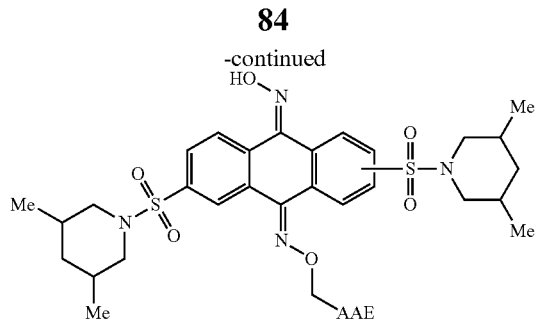

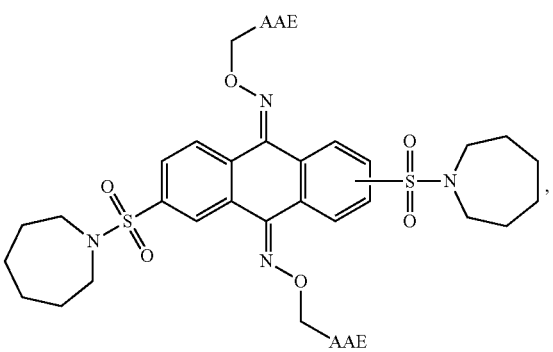

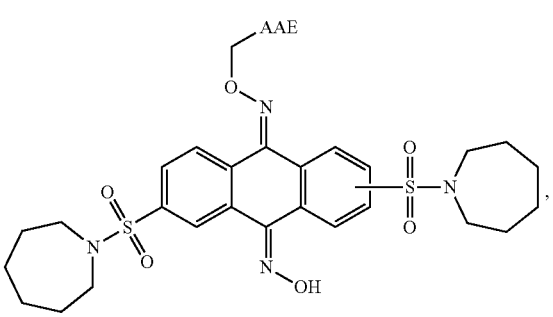

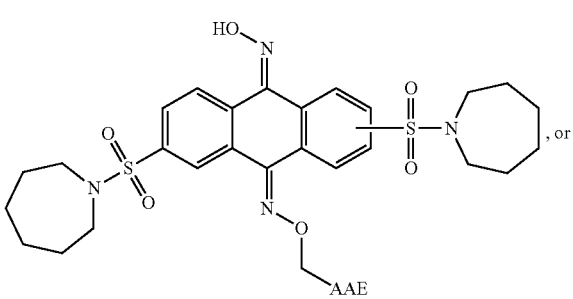

a geometric isomer, a stereoisomer, an enantiomer, a diastereomer, an ester, a tautomer, or a pharmaceutically acceptable salt thereof, wherein AAE is an Amino Acid Ester selected from both natural and unnatural aminoacids.

8. The compound of claim 7, wherein AAE is selected from the group consisting of Glycine, L-Alanine, L-Valine, D-Valine, L-Serine, L-Cysteine, L-Leucine, L-Isoleucine, L-Lysine, L-Phenylalanine, L-Proline, L-Tyrosine and L-Serine.

9. The compound of claim 7, wherein said compound is selected from the group consisting of

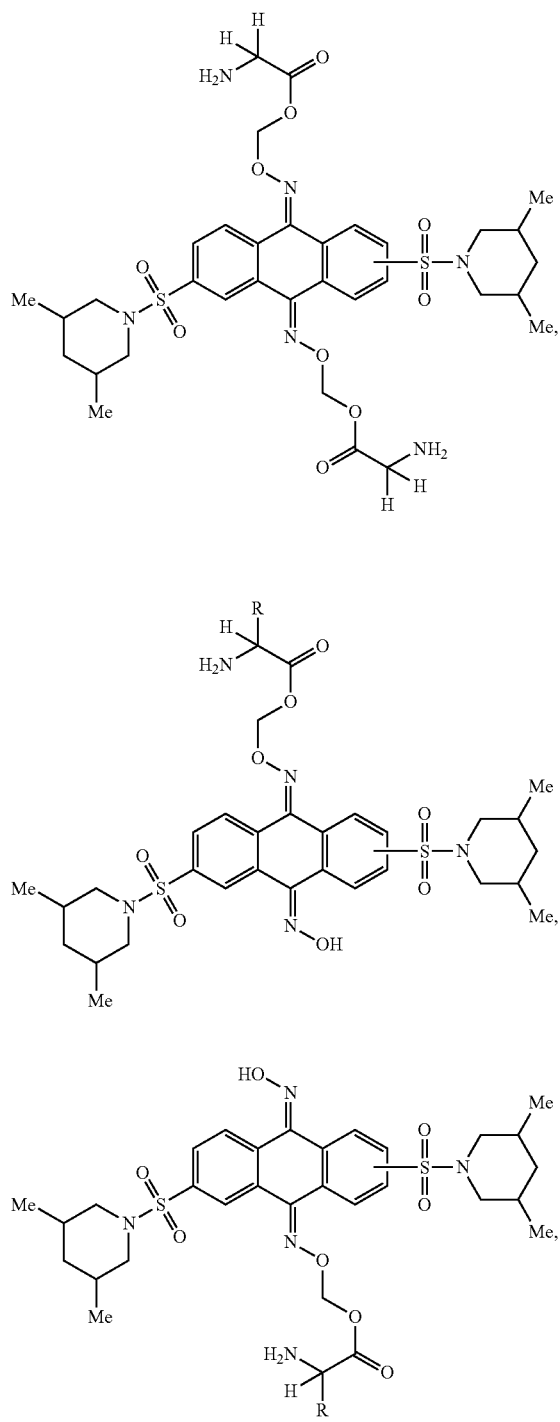
wherein R is selected from the group consisting of H, methyl, isopropyl, t-butyl, —CH₂OH, —CH₂CH(Me)₂, —CH(Me)CH₂CH₃, and
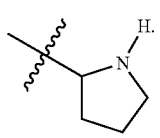
10. A compound selected from the group consisting of
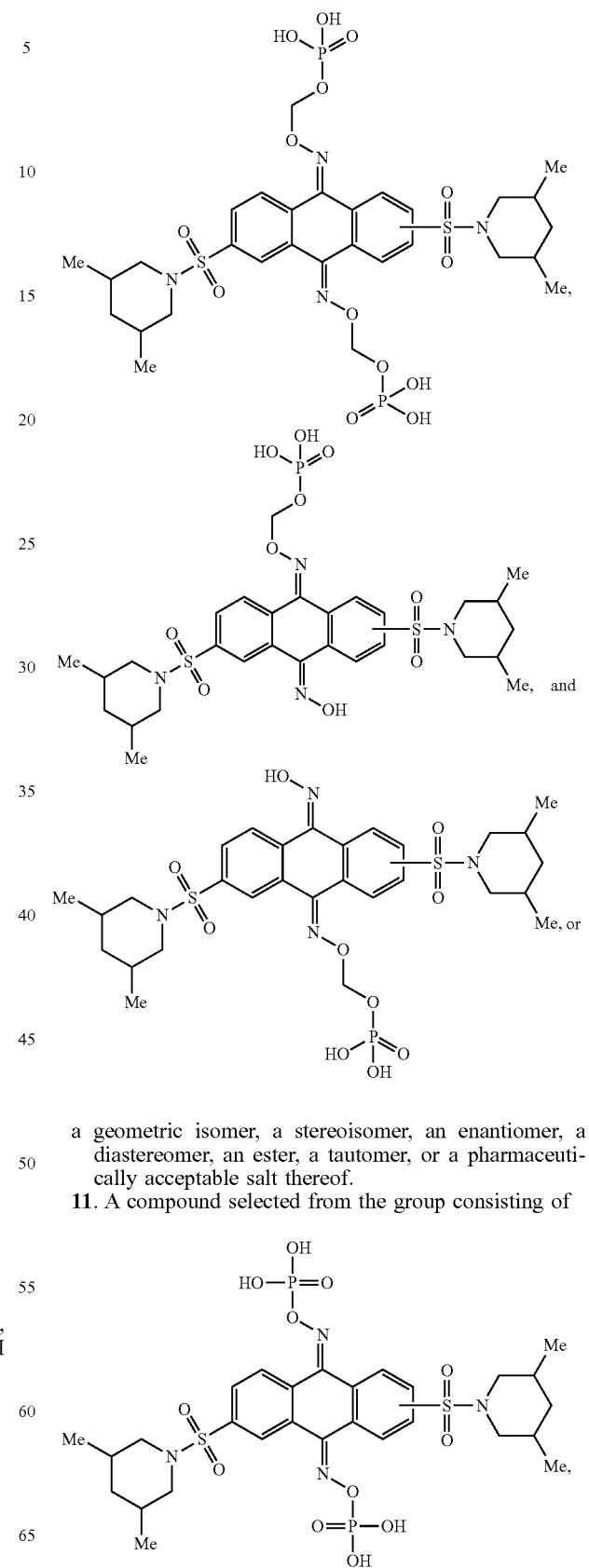
a geometric isomer, a stereoisomer, an enantiomer, a diastereomer, an ester, a tautomer, or a pharmaceutically acceptable salt thereof.
11. A compound selected from the group consisting of -continued

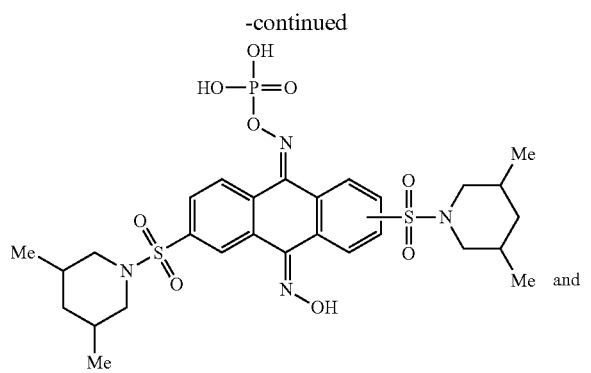

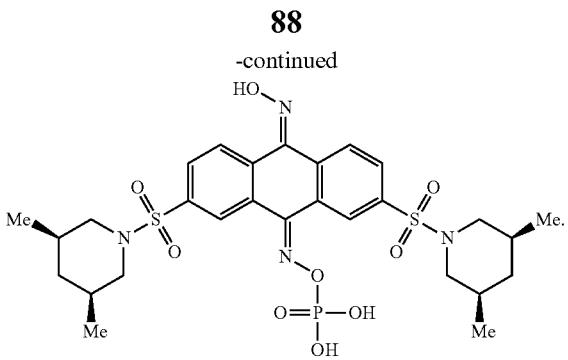

or a geometric isomer, a stereoisomer, an enantiomer, a diastereomer, an ester, a tautomer, or a pharmaceutically acceptable salt thereof.

12. The compound of claim 11, wherein said compound is selected from the group consisting of 13. The compound of claim 10, wherein said compound is selected from the group consisting of

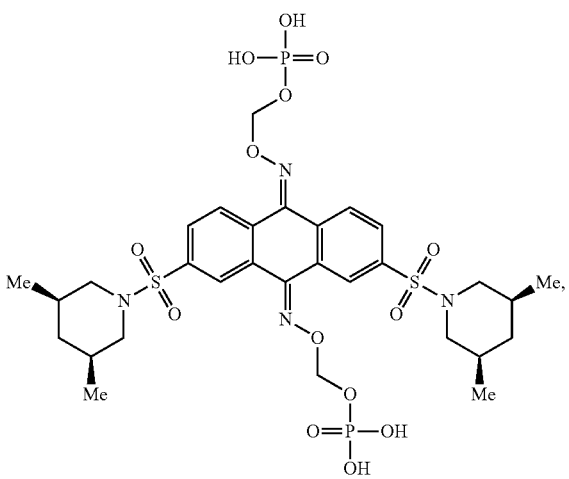

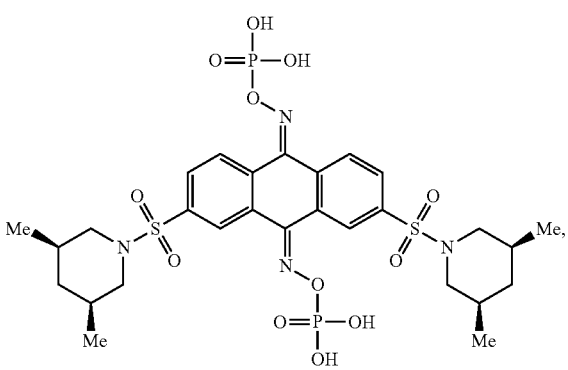

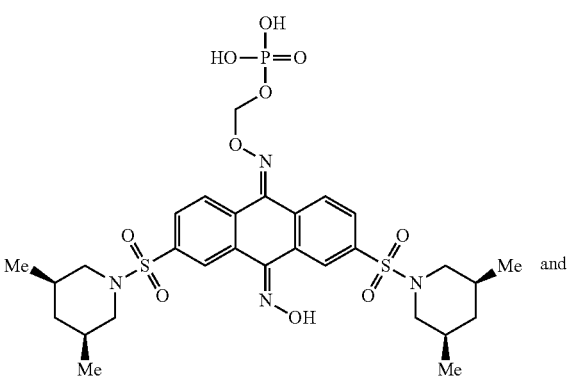

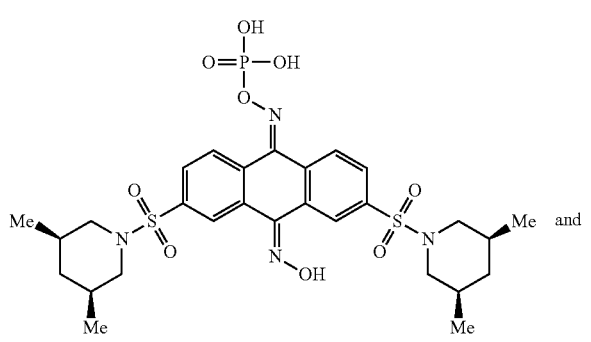

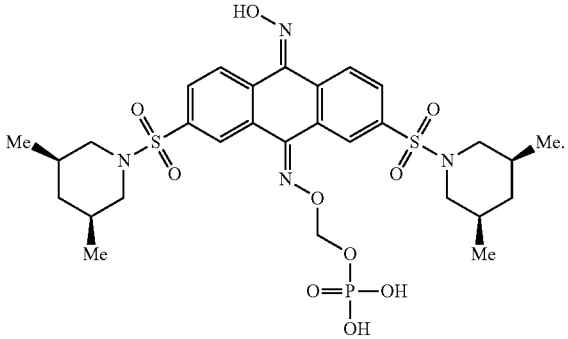

14. The compound of claim 7, wherein said compound is selected from the group consisting of

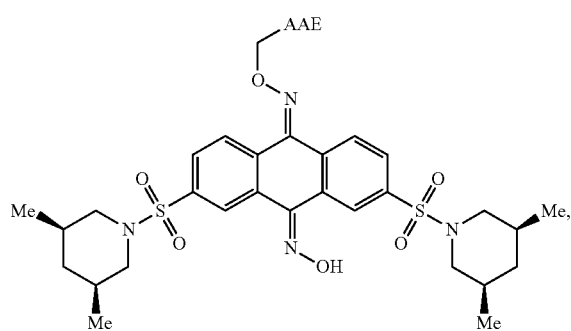
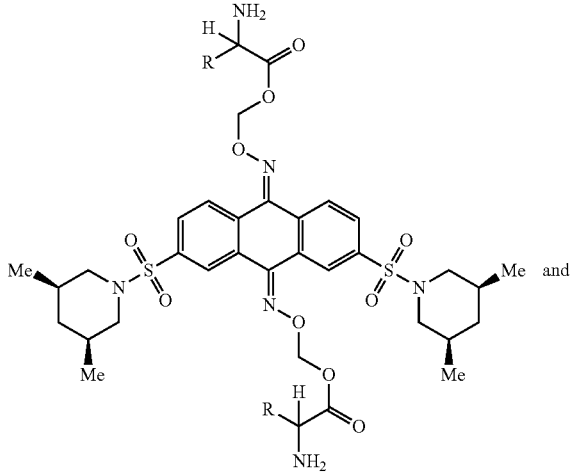
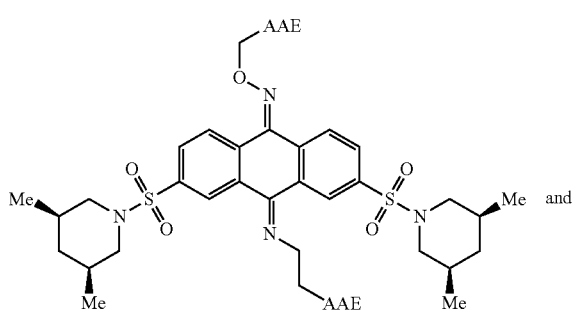
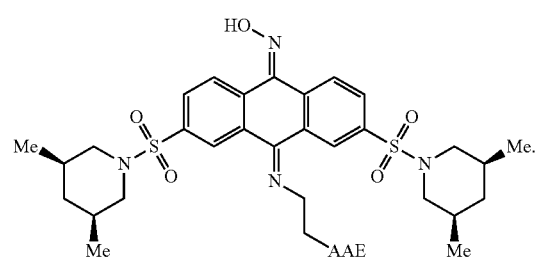
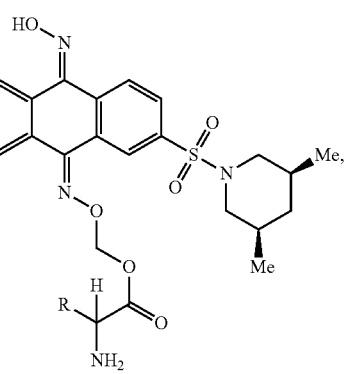
15. A compound selected from the group consisting of
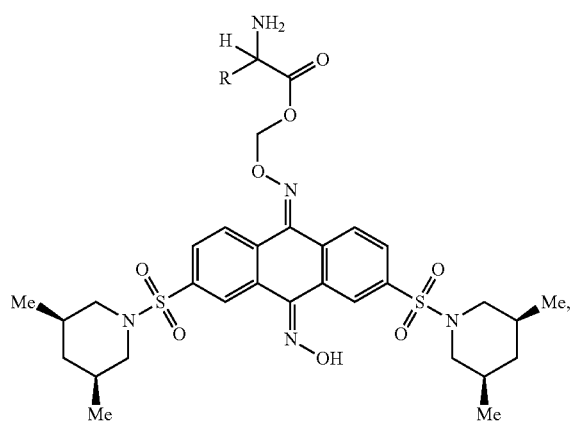
wherein R is selected from the group consisting of H, methyl, i-propyl, t-butyl, —CH$_2$OH, —CH$_2$CH(Me)$_2$, —CH(Me)CH$_2$CH$_3$, and
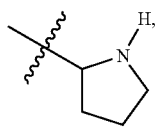
or a geometric isomer, a stereoisomer, an enantiomer, a diastereomer, an ester, a tautomer, or a pharmaceutically acceptable salt thereof.

16. A compound selected from the group consisting of

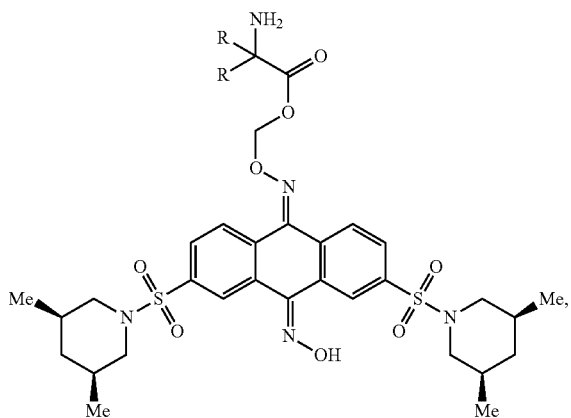

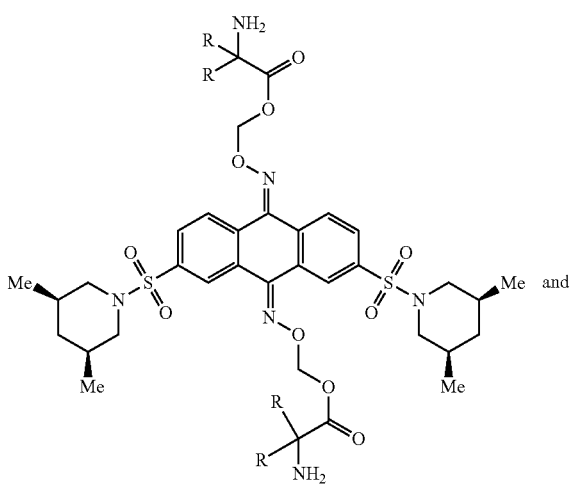

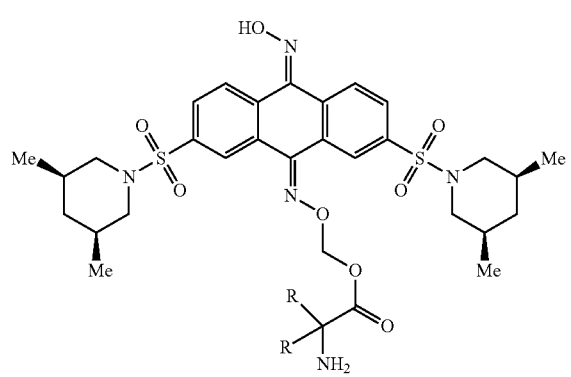

wherein R is CH₃ or ethyl, or R and R together form cyclopropyl, cyclopentyl, or pyran, or a geometric isomer, a stereoisomer, an enantiomer, a diastereomer, an ester, a tautomer, or a pharmaceutically acceptable salt thereof.

17. The compound of claim 1, wherein said compound has the following structure:

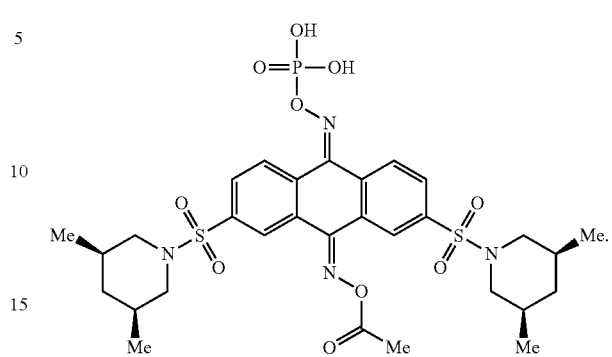

18. A compound having a structure represented by a formula (I)

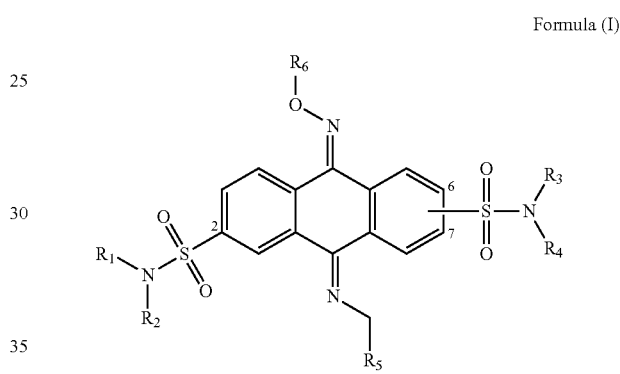

Formula (I)

or a geometric isomer, a stereoisomer, an enantiomer, a diastereomer, an ester, a tautomer, or a pharmaceutically acceptable salt thereof:
wherein
$R_1$, $R_2$, $R_3$, and $R_4$ are each independently selected from H, alkyl, heteroalkyl, cycloalkyl, arylcycloalkyl, alkenyl, alkynyl, aryl, heteroaryl, heterocycloalkyl, and each of said $NR_1R_2$ and $NR_3R_4$ can independently combine to form a 6- to 15-membered heterocycloalkyl;
$R_5$ is selected from the group consisting of —P(O)(OH)₂, —CHR₇—O—P(O)(OH)₂, —C(O)—R₈, and —CHR₇—O—C(O)—R₈,
$R_6$ is selected from the group consisting of H, —P(O)(OH)₂; CHR₇—O—P(O)(OH)₂, —C(O)—R₈, and —CHR₇—O—C(O)—R₈,
$R_7$ is H or an optionally substituted lower alkyl;
$R_8$ is a lower alkyl, —OR₁₁, -aryl, heteroaryl or heterocycloalkyl, wherein said lower alkyl, aryl, heteroaryl or heterocycloalkyl is optionally substituted with —NR₉R₁₀ and/or OR₁₂;
$R_9$ and $R_{10}$ are independently selected from the group consisting of H, —P(O)(OH)₂, and optionally substituted lower alkyl;
$R_{11}$ is independently selected from the group consisting of lower alkyl, aryl, heteroaryl and heterocycloalkyl wherein said lower alkyl, aryl, heteroaryl or heterocycloalkyl is optionally substituted with —NR₉R₁₀ and/or —OH; and
$R_{12}$ is H or —P(O)(OH)₂.

19. A method for treating cancer comprising administering to a subject in need thereof a combination of: 1) a pharmaceutically effective amount of a compound of claim 1, 7, 10, 11, 15, 16 or 18; and 2) a pharmaceutically effective amount of at least one additional anti-cancer agent.

20. The method of claim 19, wherein the additional anti-cancer agent is selected from the group consisting of antimitotic agents, antimetabolite agents, HDAC inhibitors, proteosome inhibitors, immunotherapeutic agents, FLT-3 kinase inhibitors, and WNT pathway inhibitors.

21. A method of treating or ameliorating cancer or tumor metastasis in a mammal in need thereof comprising administering to said mammal an effective amount of a compound of claim 1, 7, 10, 11, 15, 16 or 18.

* * * * *